(12) United States Patent
Joshi et al.

(10) Patent No.: US 11,797,318 B1
(45) Date of Patent: Oct. 24, 2023

(54) APPARATUS, SYSTEM AND METHOD FOR WORKFLOW PROCESSING IN A MEDICAL COMPUTER SYSTEM

(71) Applicant: ALLSCRIPTS SOFTWARE, LLC, Chicago, IL (US)

(72) Inventors: Nikhil Joshi, Pune (IN); Sreemanta Dash, Bangalore (IN); David Thomas Windell, Raleigh, NC (US)

(73) Assignee: Allscripts Software, LLC, Chicago, IL (US)

( * ) Notice: Subject to any disclaimer, the term of this patent is extended or adjusted under 35 U.S.C. 154(b) by 596 days.

(21) Appl. No.: 16/203,589

(22) Filed: Nov. 28, 2018

(51) Int. Cl.
| | |
|---|---|
| *G06F 9/451* | (2018.01) |
| *H04L 67/00* | (2022.01) |
| *G06F 9/38* | (2018.01) |
| *G06F 8/38* | (2018.01) |
| *G06Q 10/0633* | (2023.01) |
| *G16H 10/20* | (2018.01) |

(52) U.S. Cl.
CPC .............. *G06F 9/451* (2018.02); *G06F 8/38* (2013.01); *G06F 9/3838* (2013.01); *G06F 9/3842* (2013.01); *G06Q 10/0633* (2013.01); *H04L 67/34* (2013.01); *G16H 10/20* (2018.01)

(58) Field of Classification Search
CPC ........ G06F 9/451; G06F 8/38; G06Q 10/0663; G16H 10/20; H04L 67/34; G06F 9/3842; G06F 9/3838
USPC .......................................................... 717/106
See application file for complete search history.

(56) References Cited

U.S. PATENT DOCUMENTS

| | | | | |
|---|---|---|---|---|
| 2004/0254465 | A1* | 12/2004 | Sano et al. ............... | A61B 8/00 600/443 |
| 2007/0244904 | A1* | 10/2007 | Durski .................... | G06F 8/30 |
| 2008/0312959 | A1* | 12/2008 | Rose et al. ............. | G16H 50/20 705/2 |
| 2009/0094074 | A1* | 4/2009 | Nikovski et al. ........ | G06F 8/10 705/7.27 |
| 2010/0070950 | A1* | 3/2010 | Smith et al. ........... | G06F 9/451 717/127 |
| 2013/0030859 | A1* | 1/2013 | Jung et al. ............. | G06Q 10/06 705/7.26 |
| 2013/0297340 | A1* | 11/2013 | Van Zon et al. ..... | G06F 19/325 705/2 |
| 2015/0178129 | A1* | 6/2015 | Dube et al. .......... | G06F 9/4881 718/106 |
| 2016/0188548 | A1* | 6/2016 | Ciabarra, Jr. et al. | G06F 40/194 715/234 |
| 2016/0300024 | A1* | 10/2016 | Janssen et al. ......... | G06Q 10/06 |
| 2020/0042609 | A1* | 2/2020 | Huang et al. ..... | G06F 16/24552 |

\* cited by examiner

*Primary Examiner* — Lewis A Bullcock Jr
*Assistant Examiner* — Theodore E Hebert
(74) *Attorney, Agent, or Firm* — Peter Zura; Loza & Loza, LLP

(57) ABSTRACT

Technologies and techniques for processing a user interface (UI) associated with a multi-nodal workflow in a medical software application. A processor-based workflow logic module processes a medical software application to determine branches of the workflow, wherein each of the branches include one or more nodes configured to receive a data input and provide a corresponding data output for the medical software application during execution. Serialization is executed on at least some of the branches to determine dependencies among at least some of the nodes in the branches. Progress of the workflow is monitored during execution of the medical software application, and used to execute UI applications and/or provide feedback data associated with the monitored progress.

20 Claims, 107 Drawing Sheets

APPARATUS, SYSTEM AND METHOD FOR WORKFLOW PROCESSING IN A MEDICAL COMPUTER SYSTEM

FIELD OF TECHNOLOGY

The present disclosure is directed to technologies and techniques for workflow processing in a medical computer system. More specifically, the present disclosure is directed to processing workflow applications in a medical computer system that utilizes technologies such as Electronic Health Records (HER) and/or Electronic Medical Records (EMR).

BACKGROUND

Workflow processing may be defined as computer processing that is performed in a series of steps, where the series is determined by dependent and/or inter-dependent nodes along one or more workflow branches in the series. As inputs are received at each node, the workflow nodes in the branches may be expanded or contracted. Workflows may be configured as sequential workflows, state machine workflows and/or rules-driven workflows. During the course of a workflow execution, a computer system should detect and process the status and progress of the workflow. This information helps the computer system to monitor the workflow to provide data and/or interfaces as necessary, which promotes efficiency in the workflow. Additionally, the computer system may provide feedback to the user during workflow monitoring, which allows users to know the status of the workflow in the computer system One of the drawbacks of some current workflow systems is that they do not have accurate ways of determining workflow progress at a specific time, relative to the overall workflow. Alternately or in addition, current workflow systems do not have accurate mechanisms for predicting or estimating the number of future actions required in a workflow. These and other drawbacks reduce computer efficiency and provide inadequate feedback to users.

SUMMARY

Various apparatus, systems and methods are disclosed herein relating to workflow processing, workflow progress estimation and UI control.

In one example, a system and apparatus are disclosed for processing a user interface (UI) associated with a multi-nodal workflow in a medical software application, comprising: a memory for storing the medical software application; a processor, operatively coupled to the memory, wherein the processor is configured to generate the UI; and a workflow logic module, operatively coupled to the processor, wherein the workflow logic module is configured to (i) process the medical software application to determine branches of the workflow, wherein each of the branches comprise one or more nodes configured to receive a data input and provide a corresponding data output for the medical software application during execution, (ii) execute serialization on at least some of the branches to determine dependencies among at least some of the nodes in the branches, (iii) monitor progress of the workflow during execution of the medical software application, based on the executed serialization, and provide feedback data associated with the monitored progress, and (iv) process the determined branches of the workflow to identify non-reachable branches to remove the non-reachable branches during further monitoring, and update the UI in accordance with the monitored progress. The workflow logic module may be configured to execute serialization on the at least some of the branches by executing a depth-first serialization or breadth-first serialization.

In other examples, a processor-based method is disclosed for processing a user interface (UI) associated with a multi-nodal workflow in a medical software application, comprising: storing the medical software application in a memory; generating, via a processor, the UI; generating, via a workflow logic module, the medical software application to determine branches of the workflow, wherein each of the branches comprise one or more nodes configured to receive a data input and provide a corresponding data output for the medical software application during execution; executing, via the workflow logic module, serialization on at least some of the branches to determine dependencies among at least some of the nodes in the branches; monitoring, via the workflow logic module, progress of the workflow during execution of the medical software application, based on the executed serialization, and provide feedback data associated with the monitored progress; and processing, via the workflow logic module, the determined branches of the workflow to identify non-reachable branches to remove the non-reachable branches during further monitoring, and updating the UI in accordance with the monitored progress.

BRIEF DESCRIPTION OF THE FIGURES

The present invention is illustrated by way of example and not limitation in the figures of the accompanying drawings, in which like references indicate similar elements and in which:

FIG. 11 shows a simulated screenshot of a node entry for a medical application on a processing device under an illustrative embodiment;

FIG. 13 shows one example of a simulated screenshot providing feedback for suture nodes under an illustrative embodiment;

FIG. 14 shows one example of another simulated screenshot providing feedback for suture nodes under an illustrative embodiment

DETAILED DESCRIPTION

Various embodiments will be described herein below with reference to the accompanying drawings. In the following description, well-known functions or constructions are not described in detail since they may obscure the invention in unnecessary detail.

It will be understood that the structural and algorithmic embodiments as used herein does not limit the functionality to particular structures or algorithms, but may include any number of software and/or hardware components. In general, a computer program product in accordance with one embodiment comprises a tangible computer usable medium (e.g., hard drive, standard RAM, an optical disc, a USB drive, or the like) having computer-readable program code embodied therein, wherein the computer-readable program code is adapted to be executed by a processor (working in connection with an operating system) to implement one or more functions and methods as described below. In this regard, the program code may be implemented in any desired language, and may be implemented as machine code, assembly code, byte code, interpretable source code or the like (e.g., via C, C++, C#, Java, Actionscript, Swift, Objective-C, Javascript, CSS, XML, etc.). Furthermore, the term "information" as used herein is to be understood as meaning digital information and/or digital data, and that the term "information" and "data" are to be interpreted as synonymous.

In addition, while conventional hardware components may be utilized as a baseline for the apparatuses and systems disclosed herein, those skilled in the art will recognize that he programming techniques and hardware arrangements disclosed herein, embodied on tangible mediums, are configured to transform the conventional hardware components into new machines that operate more efficiently (e.g., providing greater and/or more robust data, while using less processing overhead and/or power consumption) and/or provide improved user workspaces and/or toolbars for human-machine interaction.

Figure 1:
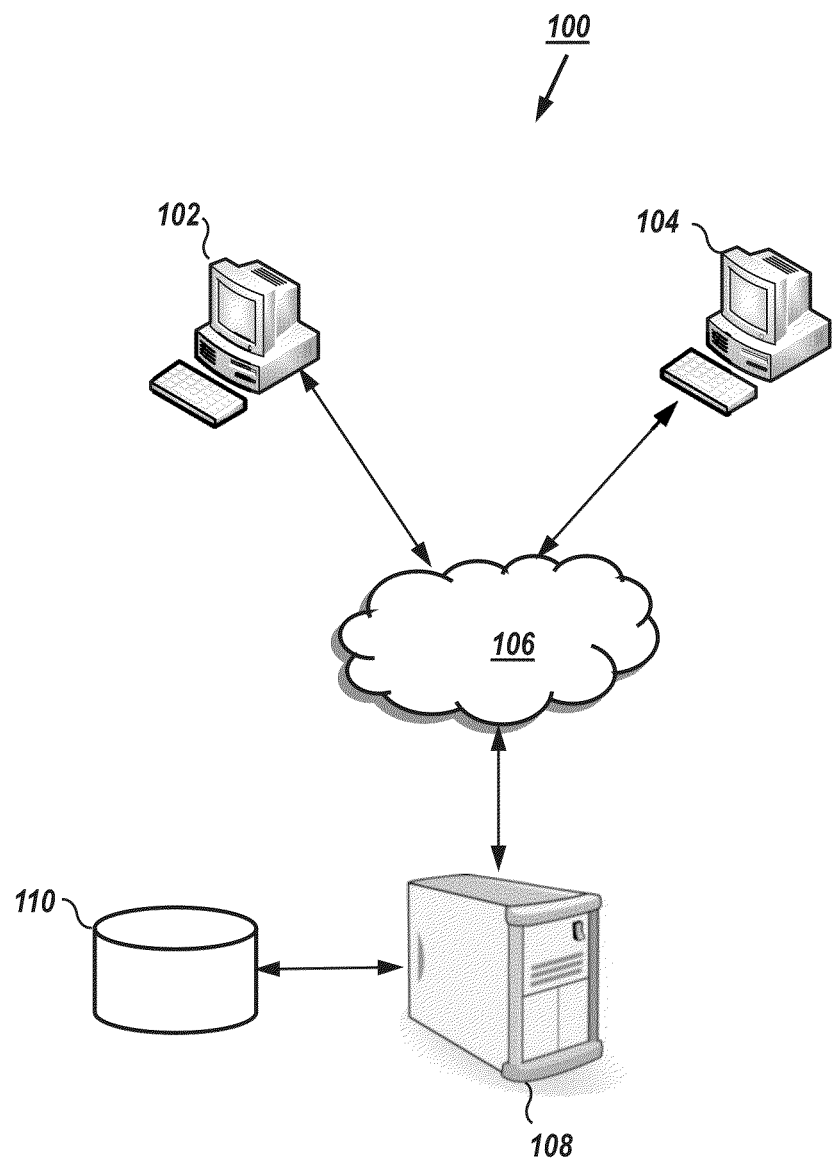
FIG. 1 illustrates a simplified overview of a processor-based computer system configured to perform workflow processing under an illustrative embodiment.

Turning to FIG. 1, a system 100 is shown for performing workflow node processing under an illustrative embodiment. The system 100 may comprise one or more computing devices (102, 104), which may be workstations, personal computers (PCs), laptops, tablets, etc., that are coupled to a computer network 106. Server 108 may also be coupled to the network 106 and communicate with any of computing devices 102, 104. While only two computing devices are shown in the figure, those skilled in the art will recognize that any number of suitable computing devices may be coupled to network 106. Similarly, server 108 may be configured as a stand-alone server, or may be part of a server network that includes a plurality of server, or a cloud server network. Server 108 may be coupled to a central storage database 110, that stores data associated with user profiles, scaling data, domain data. As will be explained in further detail below, the data from database 110, and/or data from computing devices 102, 104 may be processed to provide domain-specific text scaling control.

Figure 2:
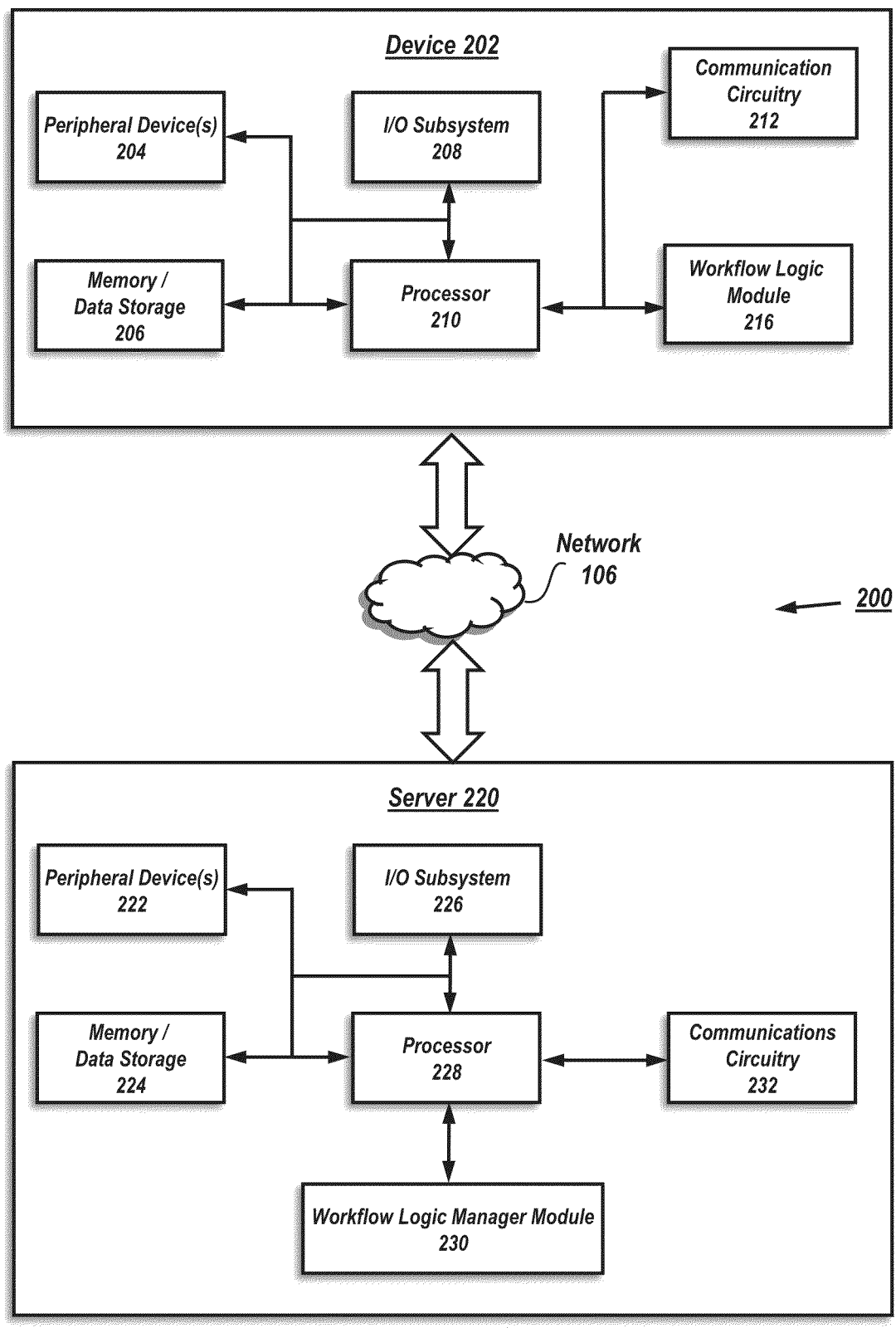
FIG. 2 schematically illustrates an operating environment for processing devices and a server communicatively coupled to a network for performing workflow processing control under an illustrative embodiment.

FIG. 2 shows an operating environment for system 200 that includes a processing device 202, which may be configured as any of computer devices 102, 104, and a server 220, which may be configured as server 108, communicating via the network 106, wherein the system is configured to provide domain-specific text scaling control under an illustrative embodiment. In the illustrative embodiment, the processing device 202 includes a processor 210 or processor circuit, one or more peripheral devices 204, memory/data storage 206, communication circuitry 212, and workflow logic module 216.

Workflow logic module 216 is configured to process workflows associated with associated software applications executed on the processing device (e.g., 202). In some illustrative embodiments, workflow logic module may process workflows to determine branches/paths and associated nodes along each branch/path. As used herein, a "branch" or "path" is defined as a sequence of executable nodes that receive data and/or input from a user. In some illustrative embodiments, the input and/or data received at a node may change direction of a branch or path, and is discussed in greater detail below (e.g., see FIGS. 4-9 and 12A-12D). The terms "branch" and "path" are intended to be synonymous. Workflow logic module 216 may further be configured to perform predictive processing on some or all branches of a workflow to estimate likely paths of a workflow. In some illustrative embodiments, workflow logic module 216 may be configured to execute serialization on workflow software prior to, or contemporaneously with execution on device 202. In some examples, the serialization may comprise depth-first and/or breadth-first serialization. The serialization may be performed on at least some of the branches to determine dependencies among at least some of the nodes in the branches.

Depth-first serialization may be used in workflow logic module 216 to traverse or search the branches of a workflow tree or graph data structures. An exemplary depth-first process starts at a root node (or a selected arbitrary node as the root node in the case of a graph or other application) and explores as far as possible along each branch before backtracking. In some applications, heuristic methods may be used for choosing a likely-looking branch. When an appropriate depth limit of a workflow tree is not known a priori, iterative deepening depth-first search may be used to apply depth-first searching repeatedly with a sequence of increasing limits. In the artificial intelligence mode of analysis, with a branching factor greater than one, iterative deepening increases the running time by only a constant factor over the case in which the correct depth limit is known due to the geometric growth of the number of nodes per level. A depth-first process may be configured as a spanning tree of the nodes (vertices) reached during the process. Based on this spanning tree, the edges of the original graph can be divided into three classes: forward edges, which point from a node of the tree to one of its descendants, back edges, which point from a node to one of its ancestors, and cross edges, which do neither. Sometimes tree edges, edges which belong to the spanning tree itself, are classified separately from forward edges. If the original graph is undirected then all of its edges may be configured as tree edges or back edges.

Breadth-first serialization may be used in workflow logic module 216 to traverse tree or graph data structures. In one example, the breadth-first serialization may begin at a tree root (or some arbitrary node of a graph, sometimes referred to as a search key), and explore all of the neighbor nodes at a present depth prior to moving on to the nodes at the next depth level. Breadth-first traversal may be accomplished by enqueueing each level of a tree sequentially as the root of any subtree is encountered. In some examples, there may be a plurality of cases in the iterative algorithm. One case may be a "root case", where the traversal queue is initially empty so the root node is added before the general case. Another case may be a "general case", where any items in the queue are processed, while also expanding their children. The process may stop if the queue is empty. In other words, the general case will halt after processing the bottom level as leaf nodes have no children.

Those skilled in the art will recognize that the present disclosure contemplates other serialization techniques known in the art, and may include alternate/additional workflow processing algorithms. In some illustrative embodiments, workflow logic module 216 may include a parser configured as a compiler or interpreter component that breaks workflow data into smaller elements for translation into another language. The parser may take input in the form of a sequence of tokens or program instructions and build a data structure in the form of a parse tree or an abstract syntax tree. The parser may be configured to perform multiple analysis, such as lexical analysis, which allows the parser to produce tokens from a stream of input string characters, which are broken into small components to form meaningful expressions. Alternately or in addition, the parser may be configured to perform syntactic analysis, to allow the parser to determine whether the generated tokens form a meaningful expression. In this example, the parse may use a context-free grammar that defines algorithmic procedures for components. These may work to form an expression and define the particular order in which tokens are to be placed. Alternately or in addition, the parser may be configured to perform semantic parsing to determine the meaning and implications of the validated expression and necessary actions are taken.

In some illustrative embodiments, workflow logic module 216 may be incorporated into memory/data storage 206 with or without a secure memory area, or may be a dedicated component, or incorporated into the processor 210. Of course, processing device 202 may include other or additional components, such as those commonly found in a digital apparatus and/or computer (e.g., sensors, various input/output devices), in other embodiments. Additionally, in some embodiments, one or more of the illustrative components may be incorporated in, or otherwise form a portion of, another component. For example, the memory/data storage 206, or portions thereof, may be incorporated in the processor 210 in some embodiments.

The processor 210 may be embodied as any type of processor currently known or developed in the future and capable of performing the functions described herein. For example, the processor 210 may be embodied as a single or multi-core processor(s), digital signal processor, microcontroller, or other processor or processing/controlling circuit. Similarly, memory/data storage 206 may be embodied as any type of volatile or non-volatile memory or data storage currently known or developed in the future and capable of performing the functions described herein. In operation, memory/data storage 206 may store various data and software used during operation of the processing device 210 such as access permissions, access parameter data, operating systems, applications, programs, libraries, and drivers.

Memory/data storage 206 may be communicatively coupled to the processor 210 via an I/O subsystem 208, which may be embodied as circuitry and/or components to facilitate input/output operations with the processor 210, memory/data storage 206, and other components of the processing device 202. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 210, memory/data storage 206, and other components of the processing device 202, on a single integrated circuit chip.

The processing device 202 includes communication circuitry 212 (communication interface) that may include any number of devices and circuitry for enabling communications between processing device 202 and one or more other external electronic devices and/or systems. Similarly, peripheral devices 204 may include any number of additional input/output devices, interface devices, and/or other peripheral devices. The peripheral devices 204 may also include a display, along with associated graphics circuitry and, in some embodiments, may further include a keyboard, a mouse, audio processing circuitry (including, e.g., amplification circuitry and one or more speakers), and/or other input/output devices, interface devices, and/or peripheral devices.

The server 220 may be embodied as any type of server (e.g., a web server, etc.) or similar computing device capable of performing the functions described herein. In the illustrative embodiment of FIG. 2 the server 220 includes a processor 228, an I/O subsystem 226, a memory/data storage 224, communication circuitry 232, and one or more peripheral devices 222. Components of the server 220 may be similar to the corresponding components of the processing device 202, the description of which is applicable to the corresponding components of server 220 and is not repeated herein for the purposes of brevity.

The communication circuitry 232 of the server 220 may include any number of devices and circuitry for enabling communications between the server 220 and the processing device 202. In some embodiments, the server 220 may also include one or more peripheral devices 222. Such peripheral devices 222 may include any number of additional input/output devices, interface devices, and/or other peripheral devices commonly associated with a server or computing device. In some illustrative embodiments, the server 220 also includes a workflow logic manager module 230 that may communicate data with workflow logic module 216 from device 202. This data may in real-time as it is executed on device 202, or may be batch processed and/or pushed or otherwise transmitted at predetermined intervals. Workflow logic manager module 230 may also be configured to communicate with multiple processing devices (e.g., 102, 104) and provide workflow processing algorithms to each device, thus operating as a central manager of each workflow logic module.

In the illustrated embodiment, communication between the server 220 and the processing device 202 takes place via the network 106 that may be operatively coupled to one or more network switches (not shown). In one embodiment, the network 106 may represent a wired and/or wireless network and may be or include, for example, a local area network (LAN), personal area network (PAN), storage area network (SAN), backbone network, global area network (GAN), wide area network (WAN), or collection of any such computer networks such as an intranet, extranet or the Internet (i.e., a global system of interconnected network upon which various applications or service run including, for example, the World Wide Web). Generally, the communication circuitry of processing device 202 and the communication circuitry 232 of the server 220 may be configured to use any one or more, or combination, of communication protocols to communicate with each other such as, for example, a wired network communication protocol (e.g., TCP/IP), a wireless network communication protocol (e.g., Wi-Fi, WiMAX), a cellular communication protocol (e.g., Wideband Code Division Multiple Access (W-CDMA)), and/or other communication protocols. As such, the network 106 may include any number of additional devices, such as additional computers, routers, and switches, to facilitate communications between the processing device 202 and the server 220.

Figure 3:
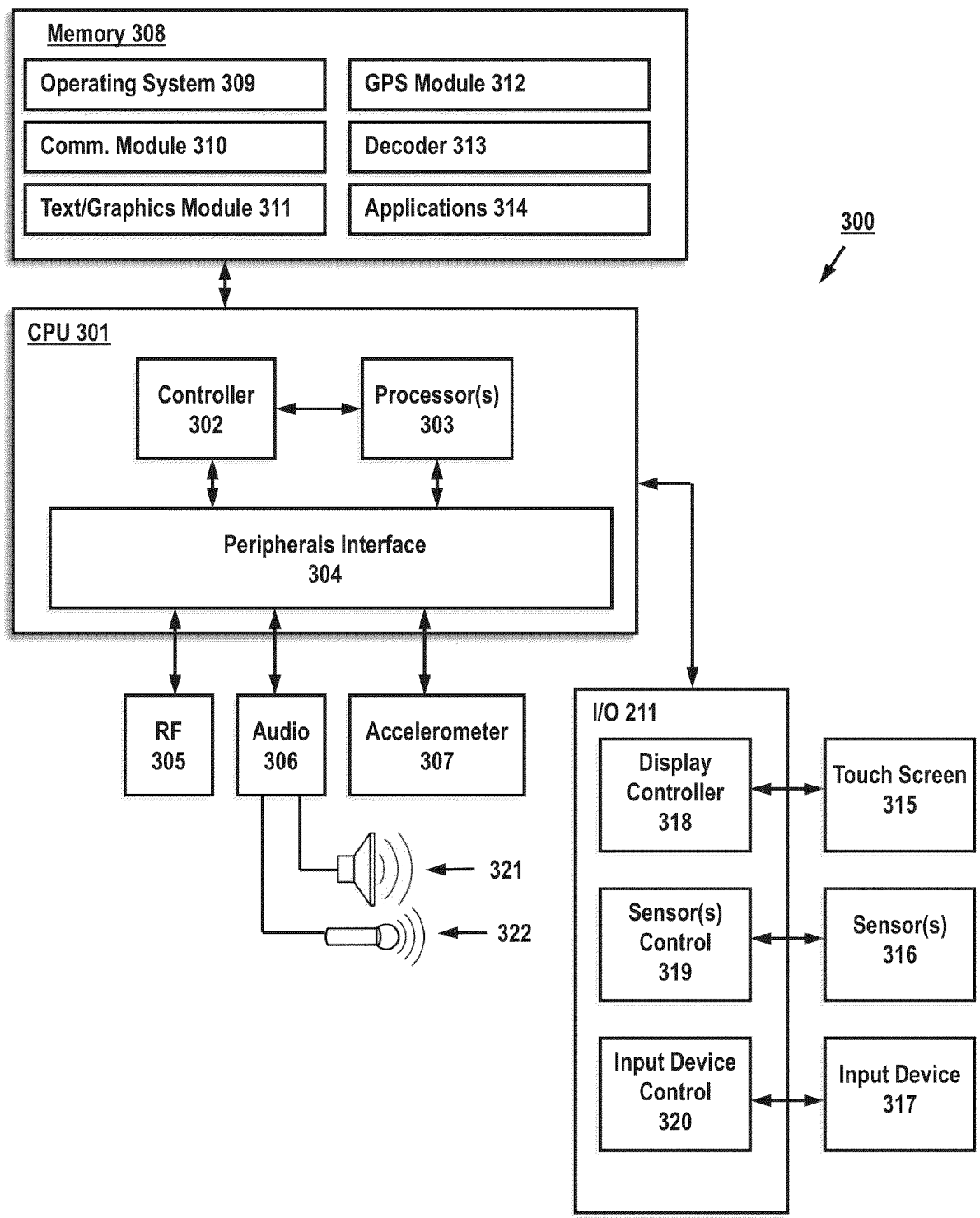
FIG. 3 schematically illustrates an operating environment for a processing device configured to perform workflow processing under an illustrative embodiment.

FIG. 3 is an exemplary embodiment of a computing device 300 (such as processing devices 102, 104), and may be a personal computer, smart phone, tablet computer, laptop and the like. Device 300 may include a central processing unit (CPU) 301 (which may include one or more computer readable storage mediums), a memory controller 302, one or more processors 303, a peripherals interface 304, RF circuitry 305, audio circuitry 306, accelerometer 307, speaker 321, microphone 322, and input/output (I/O) subsystem 221 having display controller 318, control circuitry for one or more sensors 319 and input device control 320. These components may communicate over one or more communication buses or signal lines in device 300. It should be appreciated that device 300 is only one example of a portable multifunction device, and that device 300 may have more or fewer components than shown, may combine two or more components, or a may have a different configuration or arrangement of the components. The various components shown in FIG. 3 may be implemented in hardware or a combination of hardware and software, including one or more signal processing and/or application specific integrated circuits.

Memory (or storage) 308 may include high-speed random access memory (RAM) and may also include non-volatile memory, such as one or more magnetic disk storage devices, flash memory devices, or other non-volatile solid-state memory devices. Access to memory 308 by other components of the device 300, such as processor 303, and peripherals interface 304, may be controlled by the memory controller 302. Peripherals interface 304 couples the input and output peripherals of the device to the processor 303 and memory 308. The one or more processors 303 run or execute various software programs and/or sets of instructions stored in memory 308 to perform various functions for the device 300 and to process data. In some embodiments, the peripherals interface 304, processor(s) 303, decoder 313 and memory controller 302 may be implemented on a single chip, such as a chip 301. In other embodiments, they may be implemented on separate chips.

RF (radio frequency) circuitry 305 receives and sends RF signals, also known as electromagnetic signals. The RF circuitry 305 converts electrical signals to/from electromagnetic signals and communicates with communications networks and other communications devices via the electromagnetic signals. The RF circuitry 305 may include well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 305 may communicate with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), and/or Instant Messaging and Presence Service (IMPS)), and/or Short Message Service (SMS)), or any other suitable communication protocol, including communication protocols not yet developed as of the filing date of this document.

Audio circuitry 306, speaker 321, and microphone 322 provide an audio interface between a user and the device 300. Audio circuitry 306 may receive audio data from the peripherals interface 304, converts the audio data to an electrical signal, and transmits the electrical signal to speaker 321. The speaker 321 converts the electrical signal to human-audible sound waves. Audio circuitry 306 also receives electrical signals converted by the microphone 321 from sound waves, which may include utterances from a speaker. The audio circuitry 306 converts the electrical signal to audio data and transmits the audio data to the peripherals interface 304 for processing. Audio data may be retrieved from and/or transmitted to memory 308 and/or the RF circuitry 305 by peripherals interface 304. In some embodiments, audio circuitry 306 also includes a headset jack for providing an interface between the audio circuitry 306 and removable audio input/output peripherals, such as output-only headphones or a headset with both output (e.g., a headphone for one or both ears) and input (e.g., a microphone).

I/O subsystem 221 couples input/output peripherals on the device 300, such as touch screen 315, sensors 316 and other input/control devices 317, to the peripherals interface 304. The I/O subsystem 221 may include a display controller 318, sensor controllers 319, and one or more input controllers 320 for other input or control devices. The one or more input controllers 320 receive/send electrical signals from/to other input or control devices 317. The other input/control devices 317 may include physical buttons (e.g., push buttons, rocker buttons, etc.), dials, slider switches, joysticks, click wheels, and so forth. In some alternate embodiments, input controller(s) 320 may be coupled to any (or none) of the following: a keyboard, infrared port, USB port, and a pointer device such as a mouse, an up/down button for volume control of the speaker 321 and/or the microphone 322. Touch screen 315 may also be used to implement virtual or soft buttons and one or more soft keyboards.

Touch screen 315 provides an input interface and an output interface between the device and a user. Display controller 318 receives and/or sends electrical signals from/to the touch screen 315. Touch screen 315 displays visual output to the user. The visual output may include graphics, text, icons, video, and any combination thereof. In some embodiments, some or all of the visual output may correspond to user-interface objects. Touch screen 315 has a touch-sensitive surface, sensor or set of sensors that accepts input from the user based on haptic and/or tactile contact. Touch screen 315 and display controller 318 (along with any associated modules and/or sets of instructions in memory 308) detect contact (and any movement or breaking of the contact) on the touch screen 315 and converts the detected contact into interaction with user-interface objects (e.g., one or more soft keys, icons, web pages or images) that are displayed on the touch screen. In an exemplary embodiment, a point of contact between a touch screen 315 and the user corresponds to a finger of the user. Touch screen 215 may use LCD (liquid crystal display) technology, or LPD (light emitting polymer display) technology, although other display technologies may be used in other embodiments. Touch screen 315 and display controller 318 may detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with a touch screen 315.

Device 300 may also include one or more sensors 316 such as heart rate sensors, touch sensors, optical sensors that comprise charge-coupled device (CCD) or complementary metal-oxide semiconductor (CMOS) phototransistors. The optical sensor may capture still images or video, where the sensor is operated in conjunction with touch screen display 315. Device 300 may also include one or more accelerometers 307, which may be operatively coupled to peripherals interface 304. Alternately, the accelerometer 307 may be coupled to an input controller 320 in the I/O subsystem 221. The accelerometer is preferably configured to output accelerometer data in the x, y, and z axes.

In some illustrative embodiments, the software components stored in memory 308 may include an operating system 309, a communication module 310, a text/graphics module 311, a Global Positioning System (GPS) module 312, decoder 313 and applications 314. Operating system 309 (e.g., Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components. Communication module 310 facilitates communication with other devices over one or more external ports and also includes various software components for handling data received by the RF circuitry 305. An external port (e.g., Universal Serial Bus (USB), Firewire, etc.) may be provided and adapted for coupling directly to other devices or indirectly over a network (e.g., the Internet, wireless LAN, etc.).

Text/graphics module 311 includes various known software components for rendering and displaying graphics on the touch screen 315, including components for changing the intensity of graphics that are displayed. As used herein, the term "graphics" includes any object that can be displayed to a user, including without limitation text, web pages, icons (such as user-interface objects including soft keys), digital images, videos, animations and the like. Additionally, soft keyboards may be provided for entering text in various applications requiring text input. GPS module 312 determines the location of the device and provides this information for use in various applications. Applications 314 may include various modules, including health monitoring software, sensor software, navigation software, mapping, address books/contact list, email, instant messaging, and the like.

Figure 4:
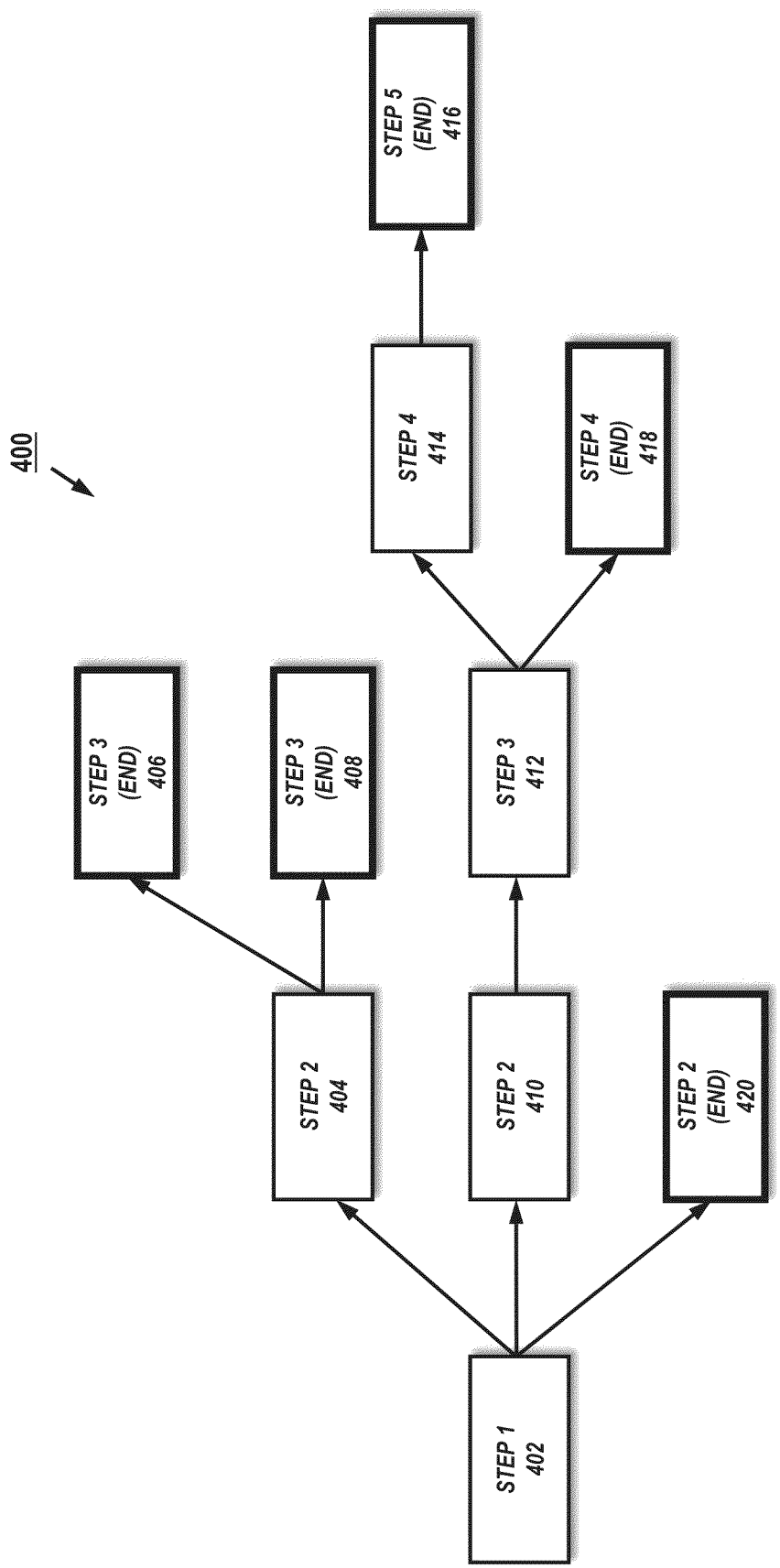
FIG. 4 shows a workflow process tree illustrating workflow steps under an illustrative embodiment.

Turning to FIG. 4, a simplified workflow process tree 400 shows a workflow process tree illustrating nodes of workflow steps under an illustrative embodiment. In this example, each block (402-416) represents executable and potentially executable steps in a computer process. The beginning of the process starts at step 1 (402), at which point, a data entry is made and/or data is received at the node (402). In this example, the node 402 is configured to accept three different data entries, where one data entry proceeds the workflow to node 404 (step 2), a second data entry proceeds the workflow to node 410 (step 2) and a third data entry proceeds the workflow to node 420 (step 2), which also results in the ending of the workflow. Thus, each of the three different data entries in node 402 result in the workflow proceeding in different branches of the workflow 400.

Turning to node 404 (step 2), the node in this example is configured to accept two different data entries, where a first data entry proceeds the workflow to node 406 (step 3), where the workflow process ends. A second data entry proceeds the workflow to node 408 (step3) where the workflow process also ends. In this example, nodes 406 and 408 both result in the ending of the workflow, but nodes 406 and 408 may be configured to provide different outputs or execute different software algorithms. Turning to node 410 (step 2), the node is configured to receive one data entry, which, when received, proceeds to node 412 (step 3). Here, node 412 is configured to accept two different data entries, where a first data entry proceeds the workflow to node 414 (step 4). Node 414 is configured to receive one data entry, which, when received, proceeds the workflow to node 416 (step 5), which ends the workflow process. When node 412 receives a second data entry, the process proceeds to node 418 (step 4), which ends to workflow process.

Thus, in the example of FIG. 4, workflow process tree 400 contains a plurality of possible node branches that may exist during execution of the workflow:

Branch 1: Step 1 (402) - Step 2 (404) → Step 3 (406) (End)
Branch 2: Step 1 (402) - Step 2 (404) → Step 3 (408) (End)
Branch 3: Step 1 (402) → Step 2 (410) → Step 3 (412) → Step 4 (414) → Step 5 (416) (End)
Branch 4: Step 1 (402) → Step 2 (410) → Step 3 (412) → Step 4 (418) (End)
Branch 5: Step 1 (402) → Step 2 (420) (End)

Again, at the end of each workflow, the processing device (e.g., 202) may be configured to provide same or different outputs and/or execute same or different software algorithms, and/or some combination.

Figure 5:
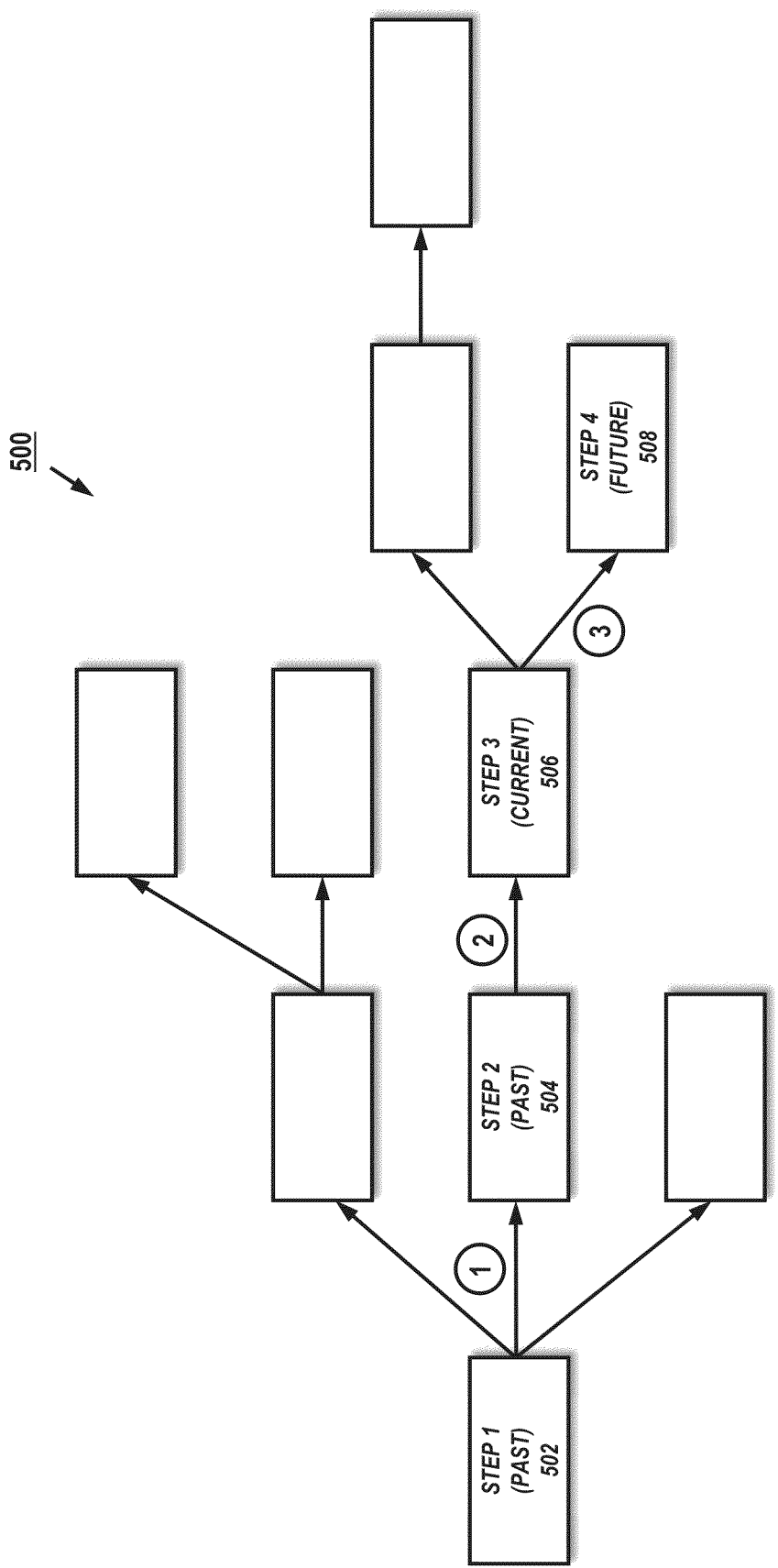
FIG. 5 shows a workflow process tree illustrating workflow steps along a workflow branch/path under an illustrative embodiment.

FIG. 5 shows a workflow process tree 500 illustrating workflow steps along a workflow branch/path under an illustrative embodiment. The workflow process tree 500 of FIG. 5 may be configured similarly to the workflow process tree 400 of FIG. 4 under an illustrative embodiment. In this example, the figured show a four-step process comprising four nodes (502-508), undergoing three node transitions (1-3) depending on specific data inputs between each node. Here, node 506 is configured as a "current" node, meaning the node in which the workflow process is currently active. As node 506 is the current node, the device, via the workflow logic module (e.g., 216) processes the workflow to determine that nodes 502 and 504 are "past" nodes, where node 504 is one step from the current node (506) and node 502 is two steps from the current node (506). Workflow logic module 216 may also process the workflow to determine that node 508 is a possible future node and that the node 508 is one step away from the current node (506) if a predetermined data entry is received.

Figure 6:
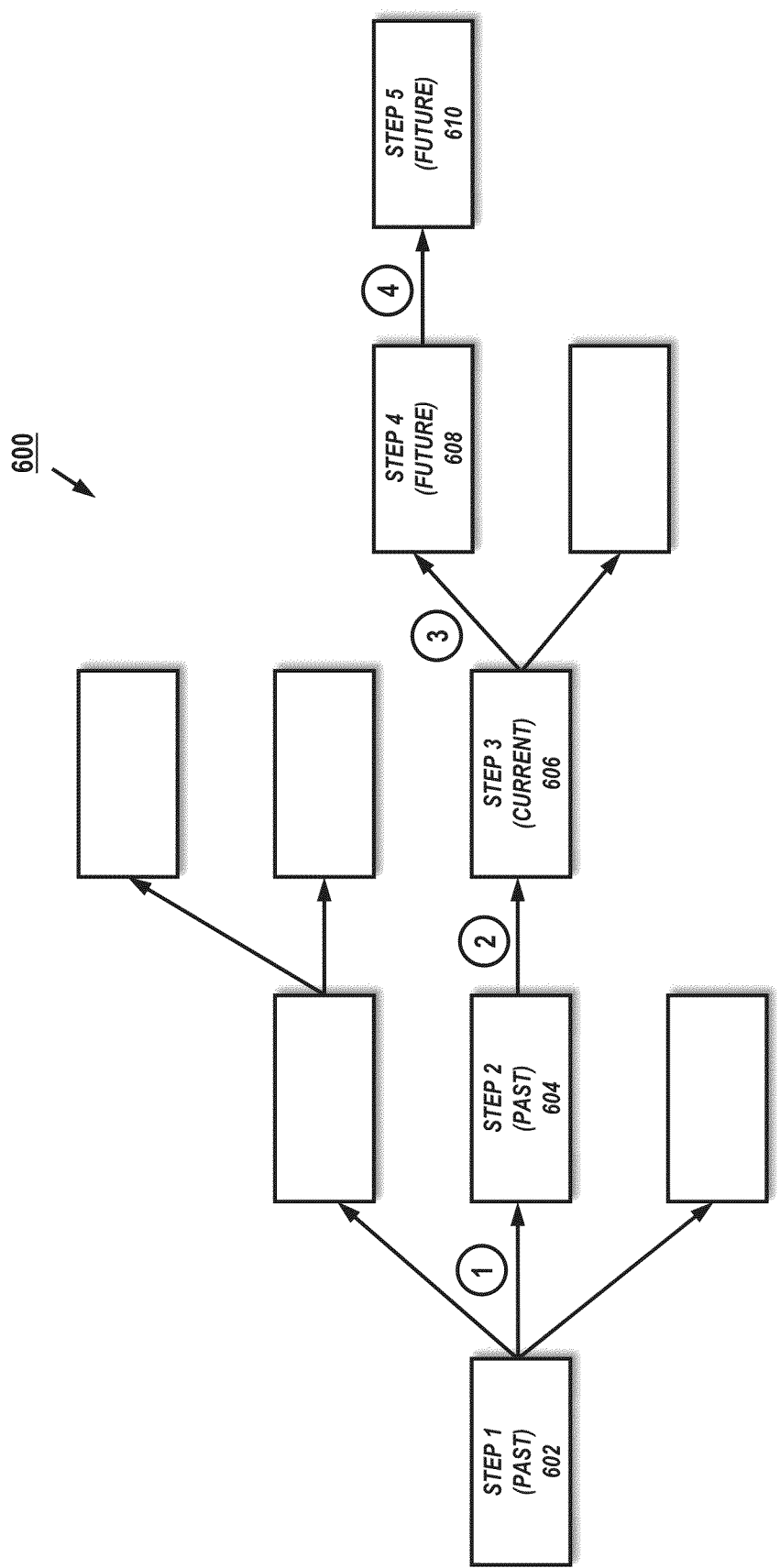
FIG. 6 shows a workflow process tree illustrating workflow steps along a another workflow branch/path, showing past, current and future nodes along the branch/path under an illustrative embodiment.

FIG. 6 shows a workflow process tree 600 illustrating workflow steps along a another workflow branch/path, showing past, current and future nodes along the branch/path under an illustrative embodiment. Workflow process tree 600 may be configured similarly to the workflow process tree 500 illustrated in FIG. 5 under an illustrative embodiment. Here, the workflow comprises a five node branch (602-610) undergoing four (1-4) node transitions depending on specific data inputs between each node during the workflow process. Here, node 606 is configured as a "current" node, meaning the node in which the workflow process is currently active. As node 606 is the current node, the device, via the workflow logic module (e.g., 216) processes the workflow to determine that nodes 602 and 604 are "past" nodes, where node 604 is one step from the current node (606) and node 602 is two steps from the current node (606). Workflow logic module 216 may also process the workflow to determine that nodes 608 and 610 are possible future node and that the node 608 is one step away from the current node (606), and node 610 is two steps away from current node 606 if a predetermined data entry is received.

Figure 7:
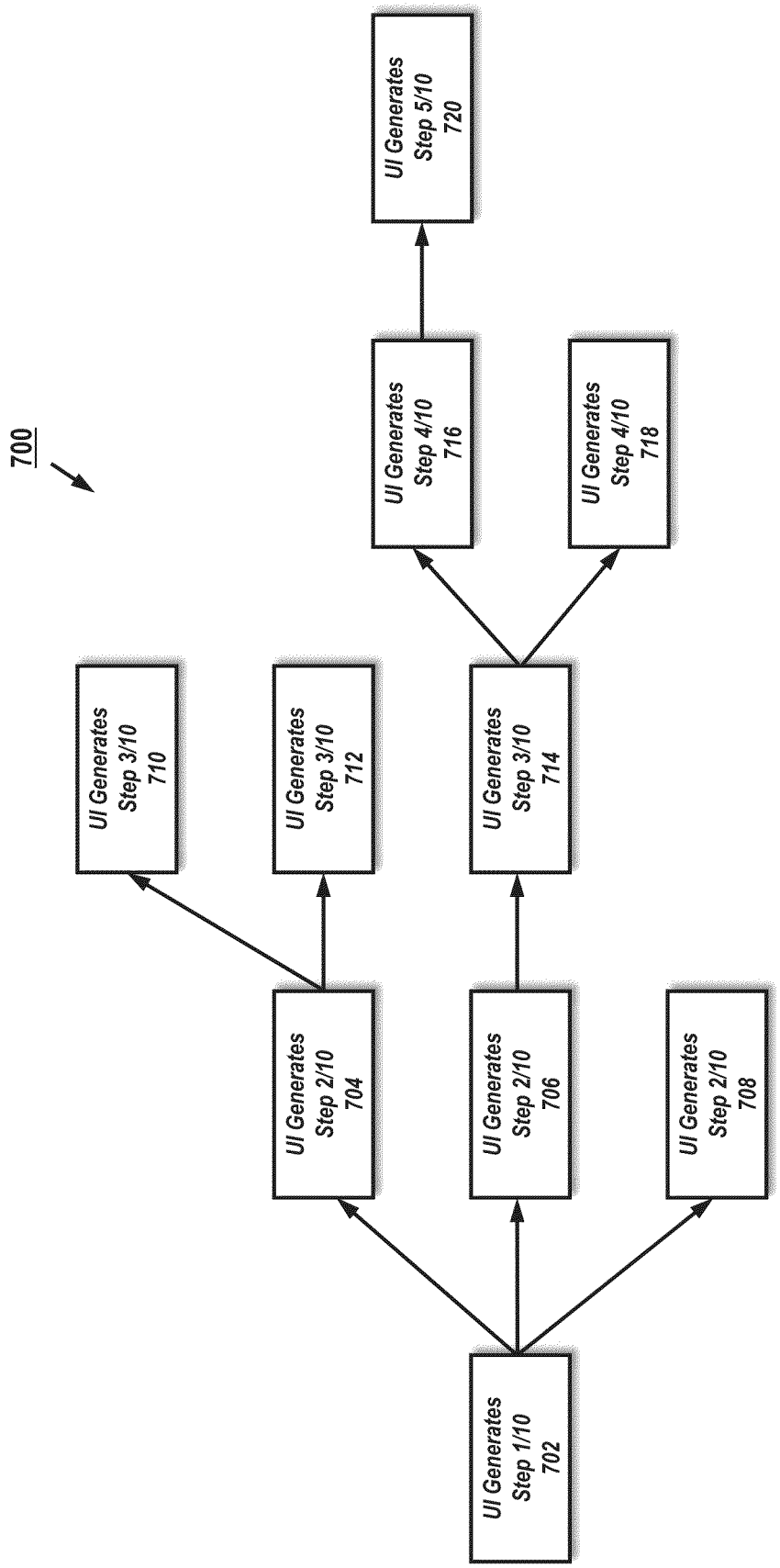
FIG. 7 shows a workflow process tree configured to calculate estimated node steps for various branches/paths of a workflow under an illustrative embodiment.

FIG. 7 shows a workflow process tree 700 configured to calculate estimated node steps for various branches/paths of a workflow under an illustrative embodiment. In this example, the nodes 702-720 are serialized to determine a total amount of possible steps (10) present among the various nodes and branches. In this example, each node 702-720 represents an output of a user interface (UI) performed at each step of each node. Additionally, each node may be identifiable as a step (e.g., 2/10, 3/10, etc.) relative to the total steps of the entire workflow.

Figure 8:
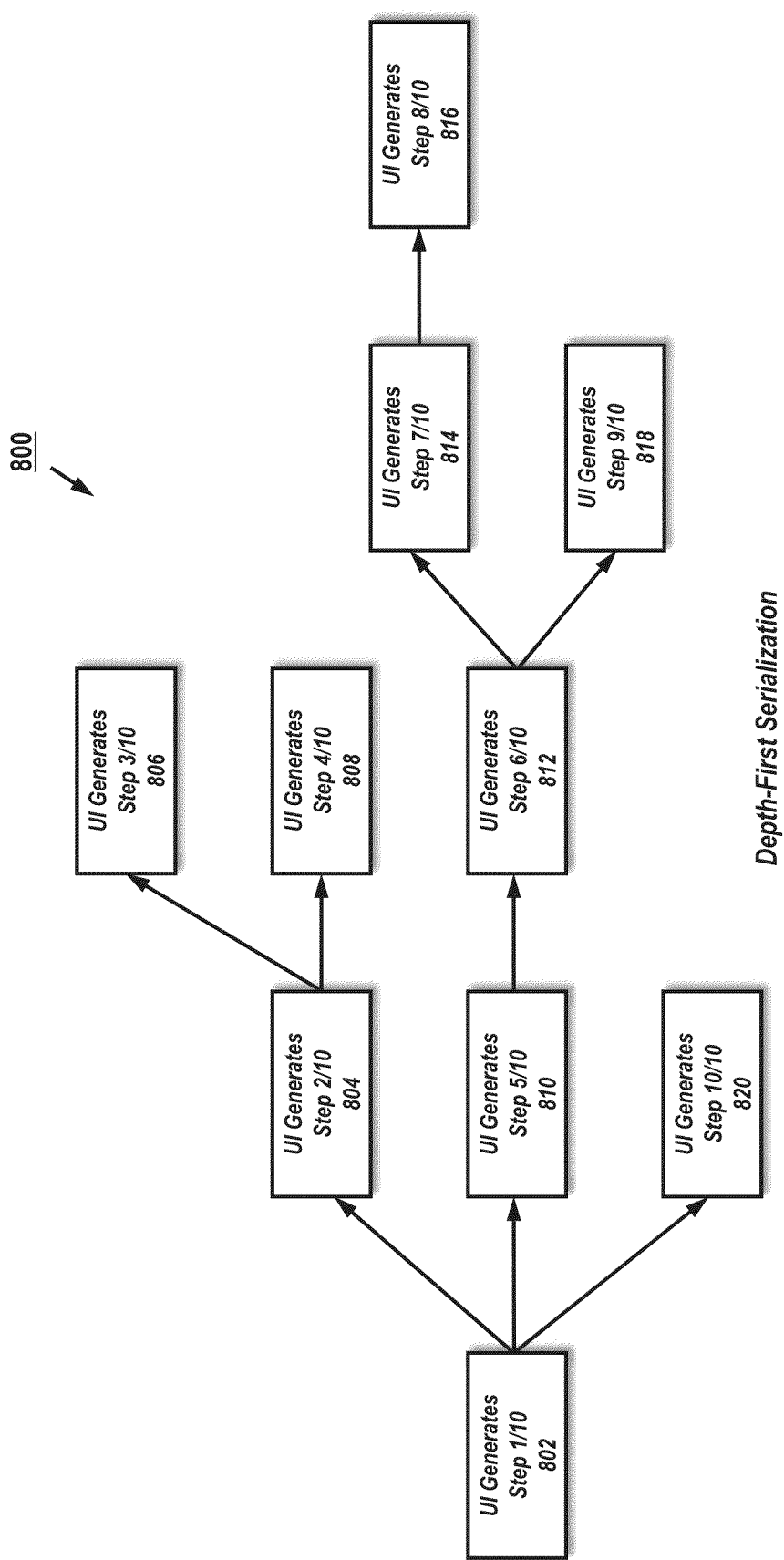
FIG. 8 shows a workflow process tree configured to calculate estimated node steps for various branches/paths of a workflow utilizing depth-first serialization under an illustrative embodiment.

FIG. 8 shows a workflow process tree 800 configured to calculate estimated node steps for various branches/paths of a workflow utilizing depth-first serialization (as discussed above in connection with FIG. 2) under an illustrative embodiment. In this example, the workflow process tree 800 is processed before operation and configured to provide a relative ratio of node steps completed versus the total number of node steps present in the workflow by serializing all steps. In the example of FIG. 8, the process begins at node 802, where a UI generates a first step (output) identified as step 1/10. The node 802 is configured to accept three different data entries, similar to the example of FIG. 4, except that the workflow process tree structure follows depth-first formatting, such that one data entry proceeds the workflow to node 804, which is formatted as step 2/10. However, a second data entry from node 802 proceeds the workflow to node 810, which is formatted as step 5/10. A third data entry from node 802 proceeds the workflow to node 820, which is formatted as step 10/10, at which point the workflow ends.

Referring back to node 804, the node is configure to accept two different data entries, where a first data entry proceeds the workflow to node 806, which is formatted as step 3/10, and where the workflow process ends. A second data entry proceeds the workflow to node 808, which is formatted as step 4/10, and where the workflow process also ends. In this example, nodes 806 and 808 both result in the ending of the workflow, but nodes 806 and 808 may be configured to provide different outputs or execute different software algorithms. Turning now to node 810 (5/10), the node is configured to receive one data entry, which, when received, proceeds to node 812 (6/10). Here, node 812 is configured to accept two different data entries, where a first data entry proceeds the workflow to node 814 (7/10). Node 814 is configured to receive one data entry, which, when received, proceeds the workflow to node 816 (8/10), which ends the workflow process. When node 812 receives a second data entry, the process proceeds to node 818 (9/10), which ends to workflow process.

Figure 9:
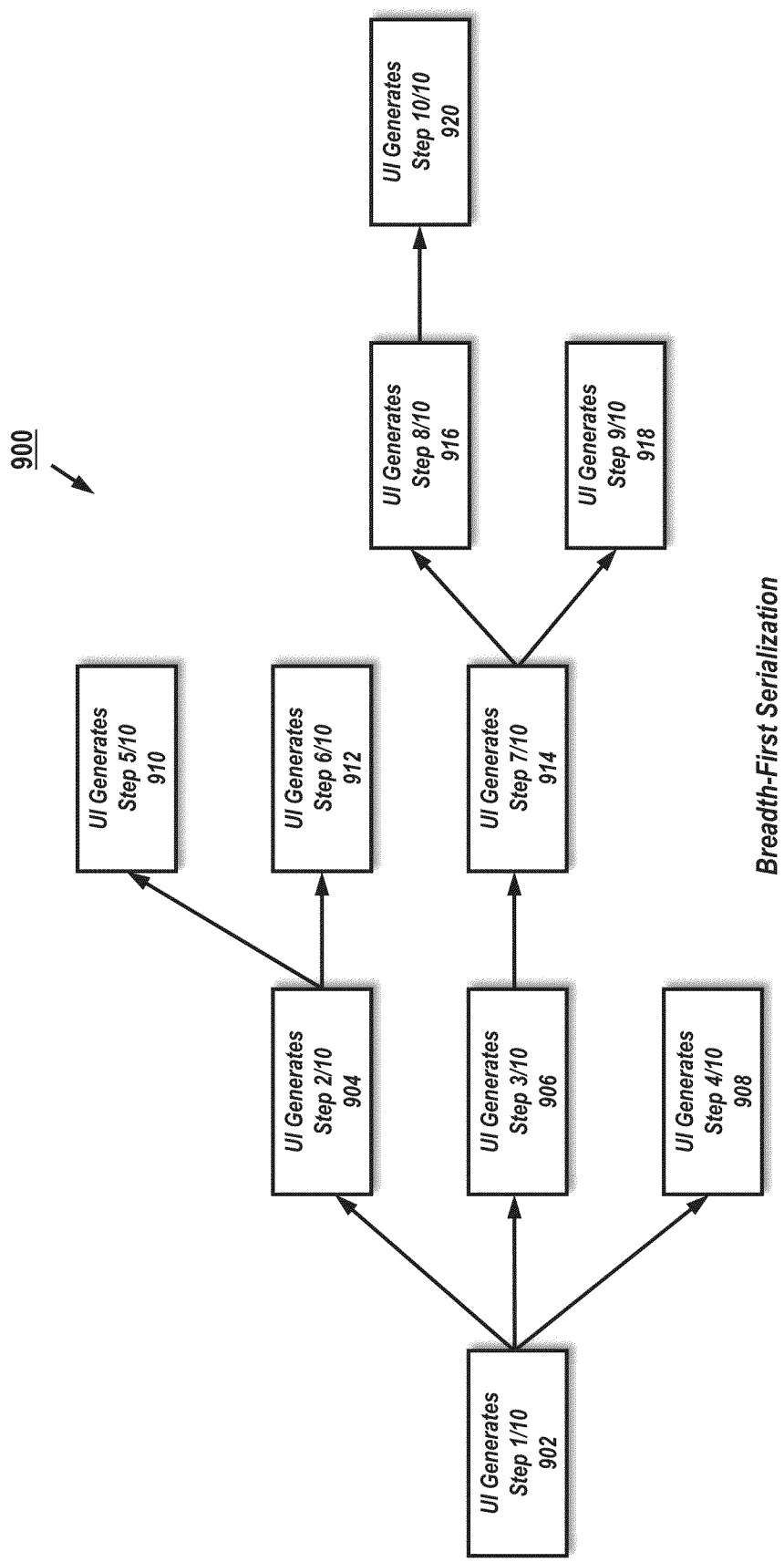
FIG. 9 shows a workflow process tree configured to calculate estimated node steps for various branches/paths of a workflow utilizing breadth-first serialization under an illustrative embodiment.

The significance of the depth-first serialization performed on the workflow process of FIG. 8 is that the workflow now has a point of reference at each node of the workflow process. For example, when the workflow process is at node 804, the processing device (e.g., 202) knows the workflow is at step 2, of 10 possible steps. However, since the process is serialized within the branch, the process knows that there is only one node remaining (806, 808), meaning that steps 3/10 (806) or 4/10 (808) result in the ending of the workflow FIG. 9 shows another workflow process tree 900 configured to calculate estimated node steps for various branches/paths of a workflow utilizing breadth-first serialization under an illustrative embodiment. Similar to the example of FIG. 8, the workflow process tree 900 is processed to serialize the tree, however, this time the serialization processing performed is breadth-first serialization. Accordingly, the nodes of FIG. 9 are arranged such that the steps are related to the level at which each node may be found. In the example of FIG. 9, node 902 may be formatted as a first level, nodes 904-908 are at a second level, nodes 910-914 are formatted at a third level, nodes 916-918 at a fourth level and node 920 at a fifth level. Under this configuration, the process may monitor and track progress throughout the workflow using the breadth-first serialization format.

Figure 10:
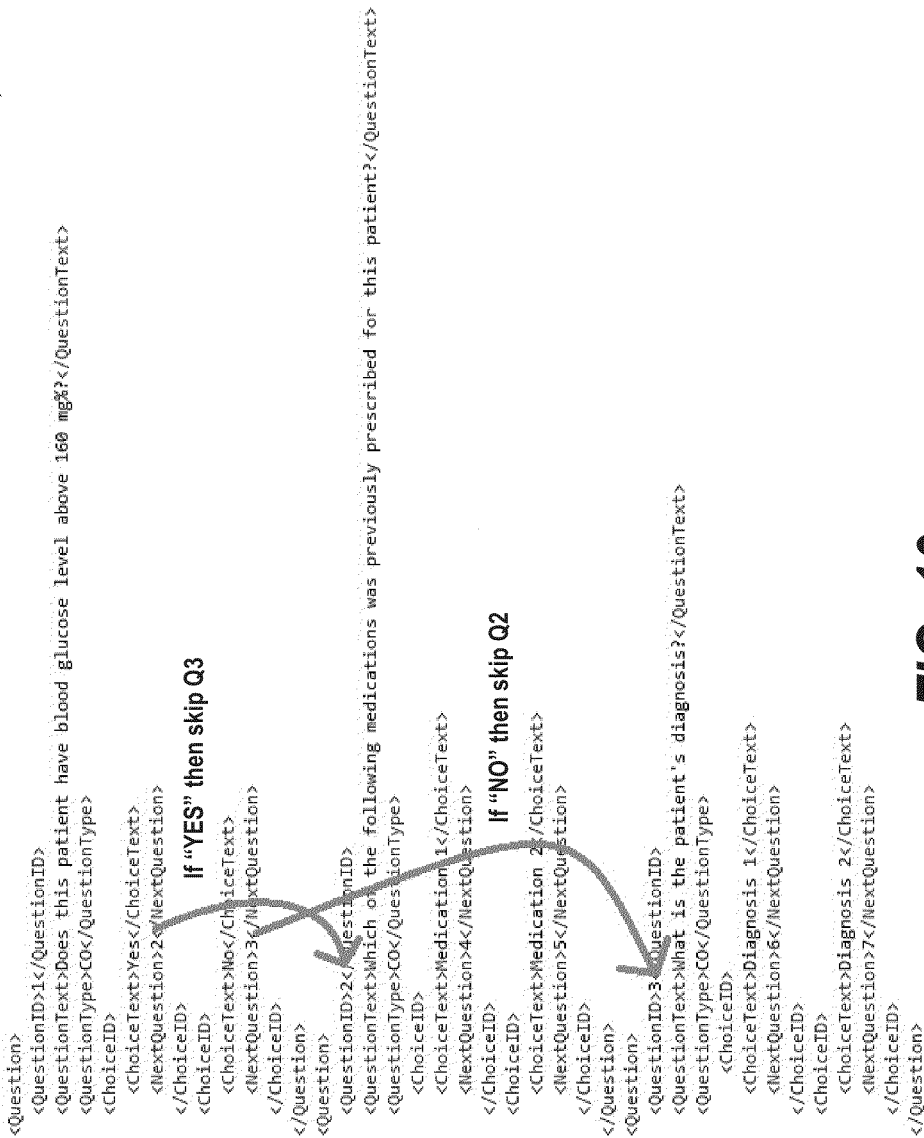
FIG. 10 shows an exemplary code sequence for serialization of nodes during a workflow under an illustrative embodiment.

The workflow trees and nodes described herein may be part of a software package, where each branch represents sequence of executable nodes that receive data and/or input from a user. The executable node may be represented as an application portion, widget, dialog box and the like. The workflows may be hard-coded in the application algorithm, or encoded in a portable file (e.g., XML). FIG. 10 shows an exemplary code sequence 1000 for serialization of nodes during a workflow under an illustrative embodiment. In this example, the code shows a sequence of requested inputs related to a medical procedure. As is appreciated in the art, medical applications often require special programming compared to common applications, as they need special and precise sequences of inputs to allow the processing device to properly and accurately provide diagnosis data for a given set of inputs. The code sequence 1000 shows an example for patient data inputs where "yes" or "no" inputs for certain questions allow the sequence to skip to other nodes (questions) to continue diagnosis. It should be understood that the example of FIG. 10 is a single, simplified, example provided for purposes of illustration and is not intended to be limiting. Similar code may be created for nodes associated with medical device software, wherein data from sensors/monitors are provided for each node. Additionally, a combination of sensor/monitor data and user input data may be utilized for nodes.

Figure 11:
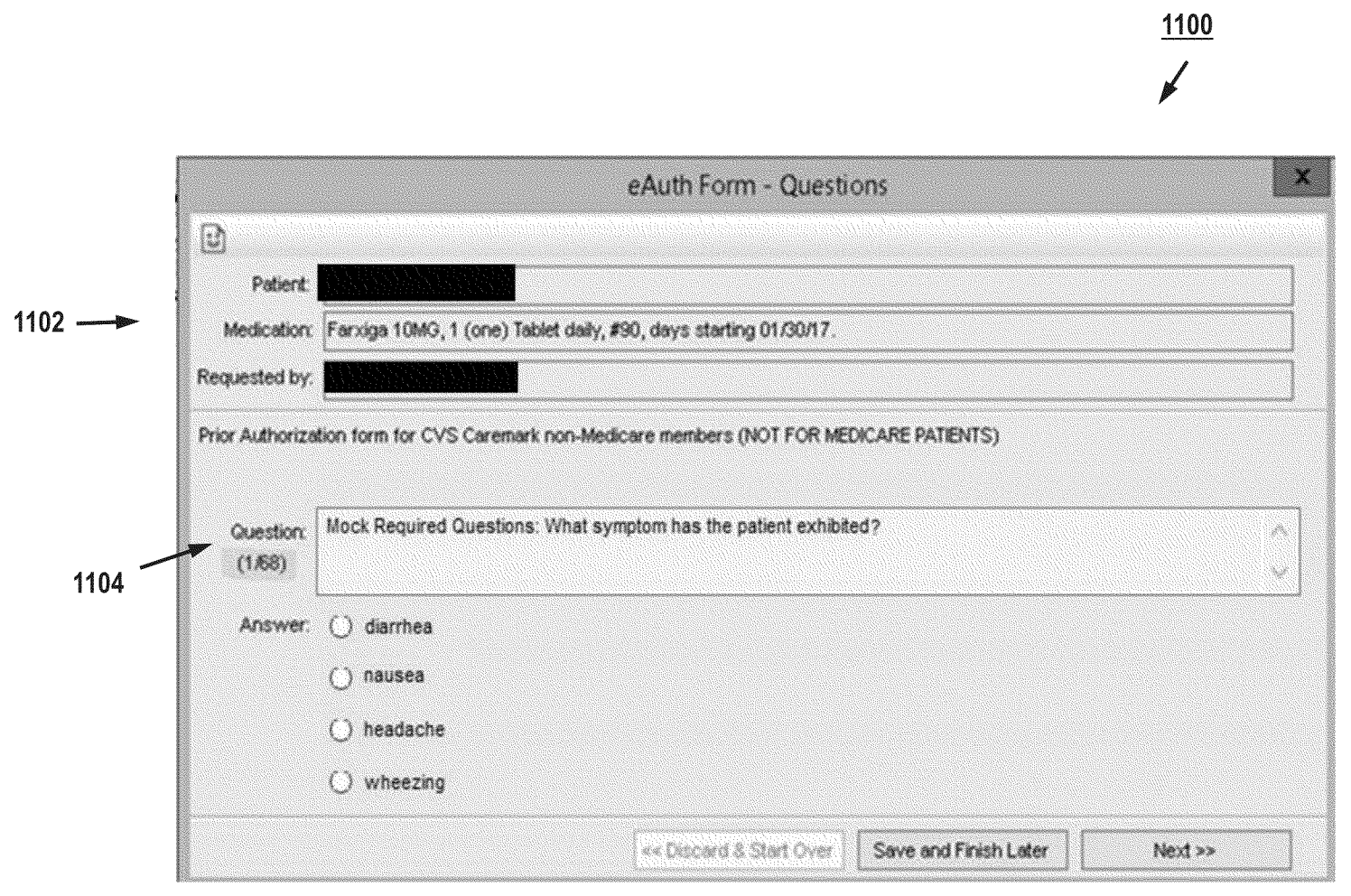

FIG. 11 shows a simulated screenshot 1100 of a node entry for a medical application on a processing device under an illustrative embodiment. In this example, a first input area 1102 is provided to associate data in the workflow to a particular patient. A second input area 1104 is provided where a data input may be received on a series of medical questions (1/68). Normally, a measure of the total pending node tasks is by displaying the unique identifier of a current step in contrast to the last unique identifier in the serialized list of the steps. In one example, the UI could display to the user that, they are on the ⅒ step, then 5/10 step, then 6/10 step, then 9/10 step and the task could terminate. However, this representation does not provide a realistic estimate of the actual remaining tasks. In a top-most path (e.g., see 802-806 of FIG. 8) a workflow may be completed just after the 3/10 step. Accordingly, under conventional operation, the system may inaccurately reflect that the workflow is still 70% incomplete.

Furthermore, as a workflow decision tree increases in possible nodes/steps, the complexity of the tree becomes exponentially more complex. For example, for a workflow comprising 68 nodes (steps), it is statistically not possible for a user to actually traverse all 68 nodes during a single workflow process, because at least one the different branches of the workflow are mutually exclusive from the others. Accordingly, technologies and techniques are also provided herein for traversing all node possibilities of a workflow in back-end, and for calculating various graph properties of the step-tree for providing a realistic estimation of the pending task to the user. Using graph theory, algorithms can be provided to calculate lengths (e.g., minimum/maximum) of a tree starting from any node, by traversing all possible routes from a current node.

Figure 12A:
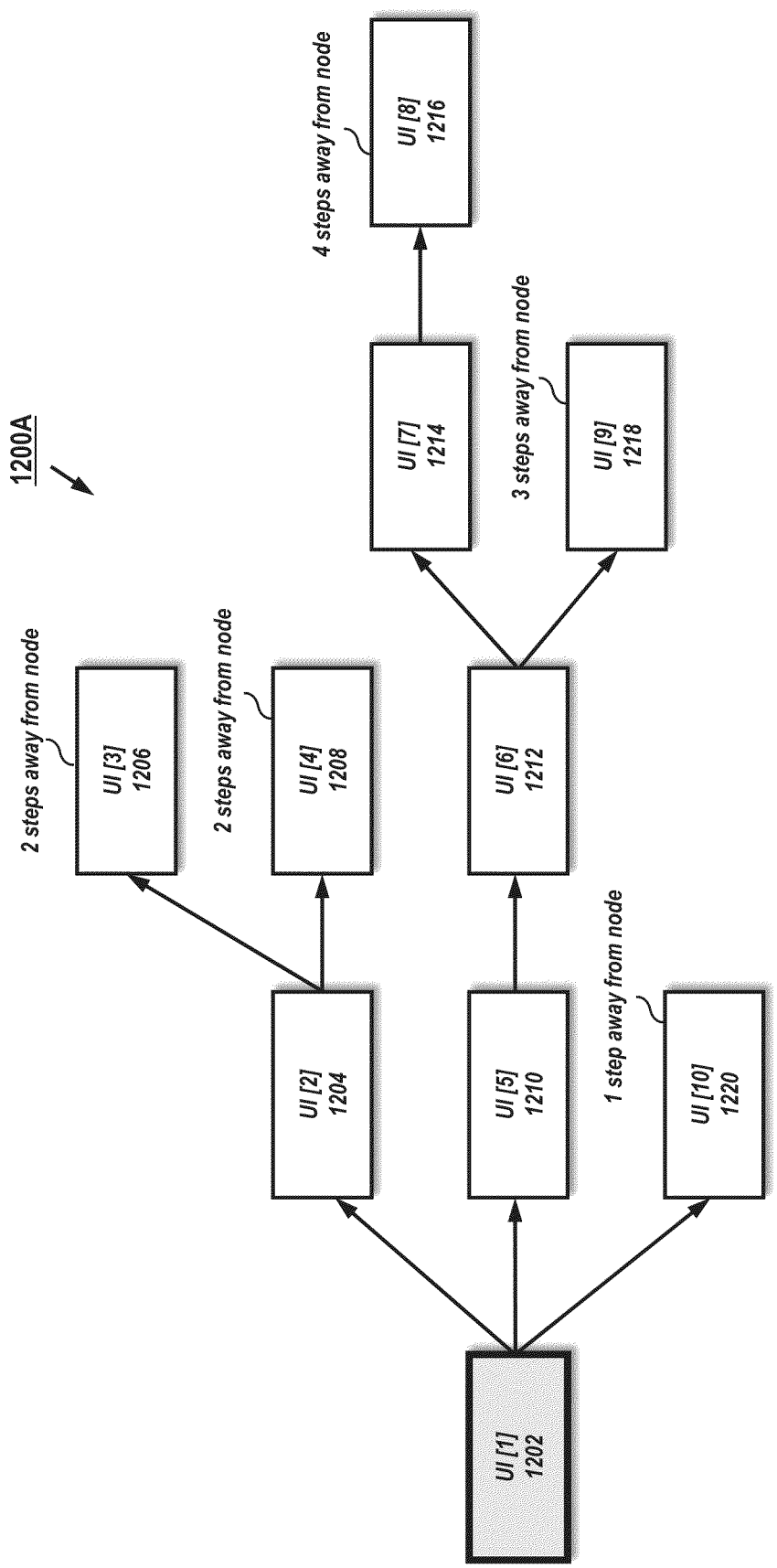
FIG. 12A shows a workflow progression with node processing under an illustrative embodiment.

Accordingly, under some illustrative embodiments, configurations may be provided where a processing device (e.g., 202) may additionally calculate a workflow node progress using more meaningful statistical analysis. Turning to FIG. 12A, the illustration shows a workflow progression with serialization and branch traversal processing under an illustrative embodiment. Here, each node 1202-1220 is represented as a user interface node (UI[1] -UI[10]) that is configured to provide a UI output and receive a data input, which moves the workflow process to a subsequent node based on the configuration of the UI node. Under the example of FIGS. 12A-12D, the workflow paths (branches) may be summarized as follows:

Path 1: UI[1] (1202) → UI[2] (1204) → UI[3] (1206) (length = 3 nodes)
Path 2: UI[1] (1202) → UI[2] (1204) → UI[4] (1208) (length = 3 nodes)
Path 3: UI[1] (1202) → UI[5] (1210) → UI[6] (1212) → UI[7] (1214) → UI[8] (1216) (length = 5 nodes)
Path 4: UI[1] (1202) → UI[5] (1210) → UI[6] (1212) → UI[9] (1218) (length = 4 nodes)
Path 5: UI[1] (1202) → UI[10] (1220) (length = 2 nodes)

As each UI receives a data input, the processing device (e.g., 202) determines one or more branches of the workflow in which the workflow may proceed. Each workflow end point (e.g., 1206, 1216, 1218, 1220) also knows a priori how many nodes or steps are required to complete the process, relative to the primary node (e.g., 1202), as shown in the figure. In addition, the processing device also determines branches of the workflow in which the process may traverse as each input is received. Similarly, the processing device may also determine which branches to discard (i.e., not reachable) from further processing. As each branch is discarded, the workflow is reprocessed to update available/ reachable nodes along the remaining branches. After creating a subset of paths possible from any current node position, the system finds the maximum and the minimum path lengths specific to that subset, and that is the minimum and the maximum number of steps that the user will need to undertake to reach the end of the workflow. As the workflow proceeds, the number of possible paths keep reducing, which in turn reduces the variation in the lengths of the possible paths which improves the accuracy of the workflow progress monitoring.

Referring to FIGS. 12A-12D, the figures will illustrate a workflow path from UI[1] through UI[9] under an illustrative embodiment. Here, the illustrative paths processed by the processing device (e.g., 202) may be shown as follows:

| Node  | Processed Calculation                  |
| ----- | -------------------------------------- |
| UI[1] | Potential 1-4 nodes after current node |
| UI[5] | Potential 2-3 nodes after current node |
| UI[6] | Potential 1-2 nodes after current node |
| UI[9] | Last node                              |

Figure 12B:
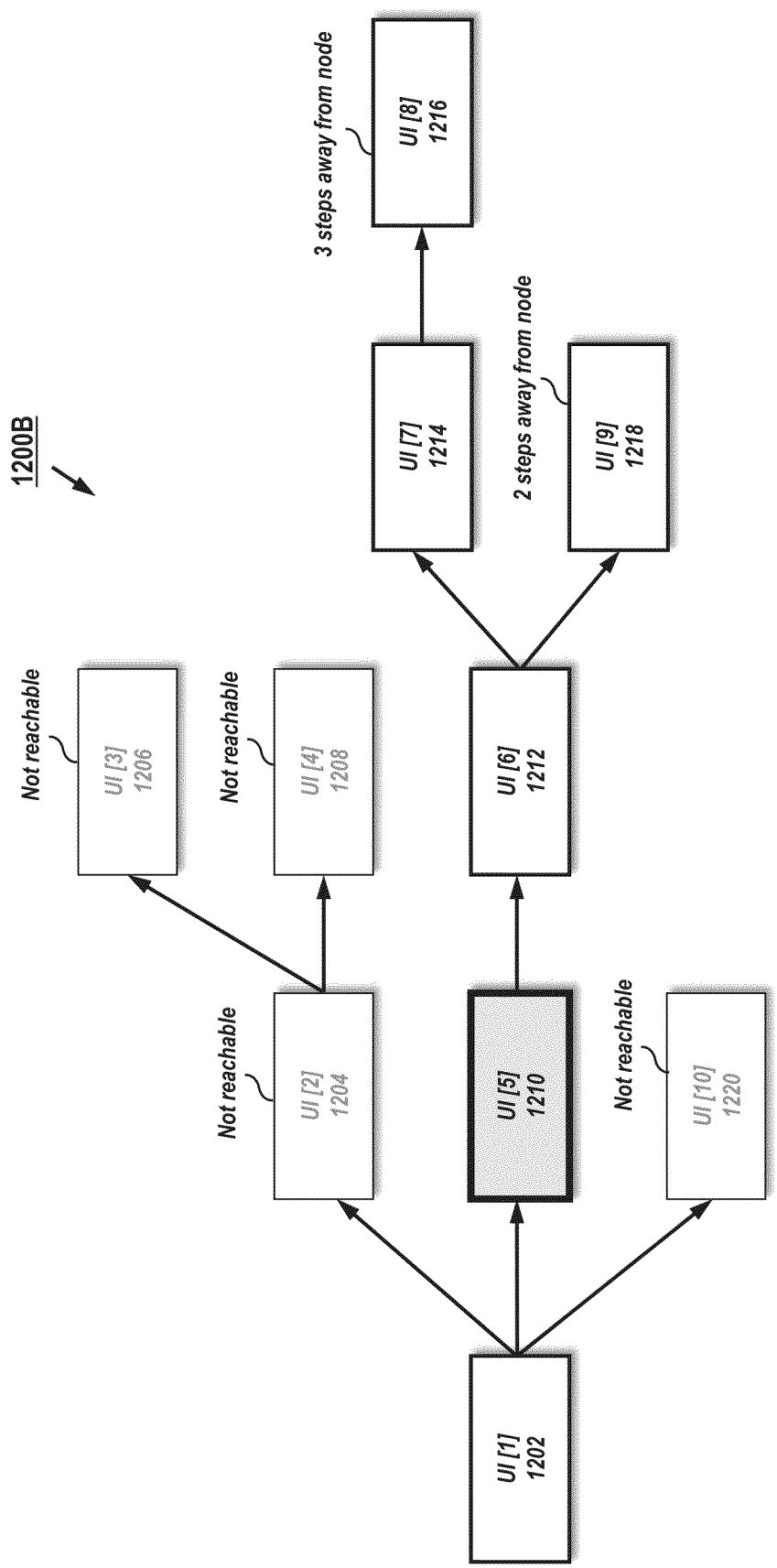
FIG. 12B show the workflow progression continuing from the embodiment of FIG. 12A with further node processing under an illustrative embodiment.

Turning now to FIG. 12B, the drawing shows the workflow progression (1200B) continuing from the embodiment of FIG. 12A with further node processing under an illustrative embodiment. Here, after UI[1] 1202 receives a certain data input, the process proceeds to node UI[5] 1210. At this point, the processing device (e.g., 202) determines that the workflow branches associated with nodes UI[2] 1204 and UI[10] 1220 are not reachable, as shown in the figure. As node UI[5] 1210 is now a current node, the processing device identifies a first branch ending at node UI[8] 1216 and may calculate that the end node UI[8] 1216 of the first branch is three steps away from the current node (1210). The processing device may also identify other branches, such as the one ending at UI[9] 1218 and calculate that the end node UI[8] 1218 is two steps away from the current node (1210).

Figure 12C:
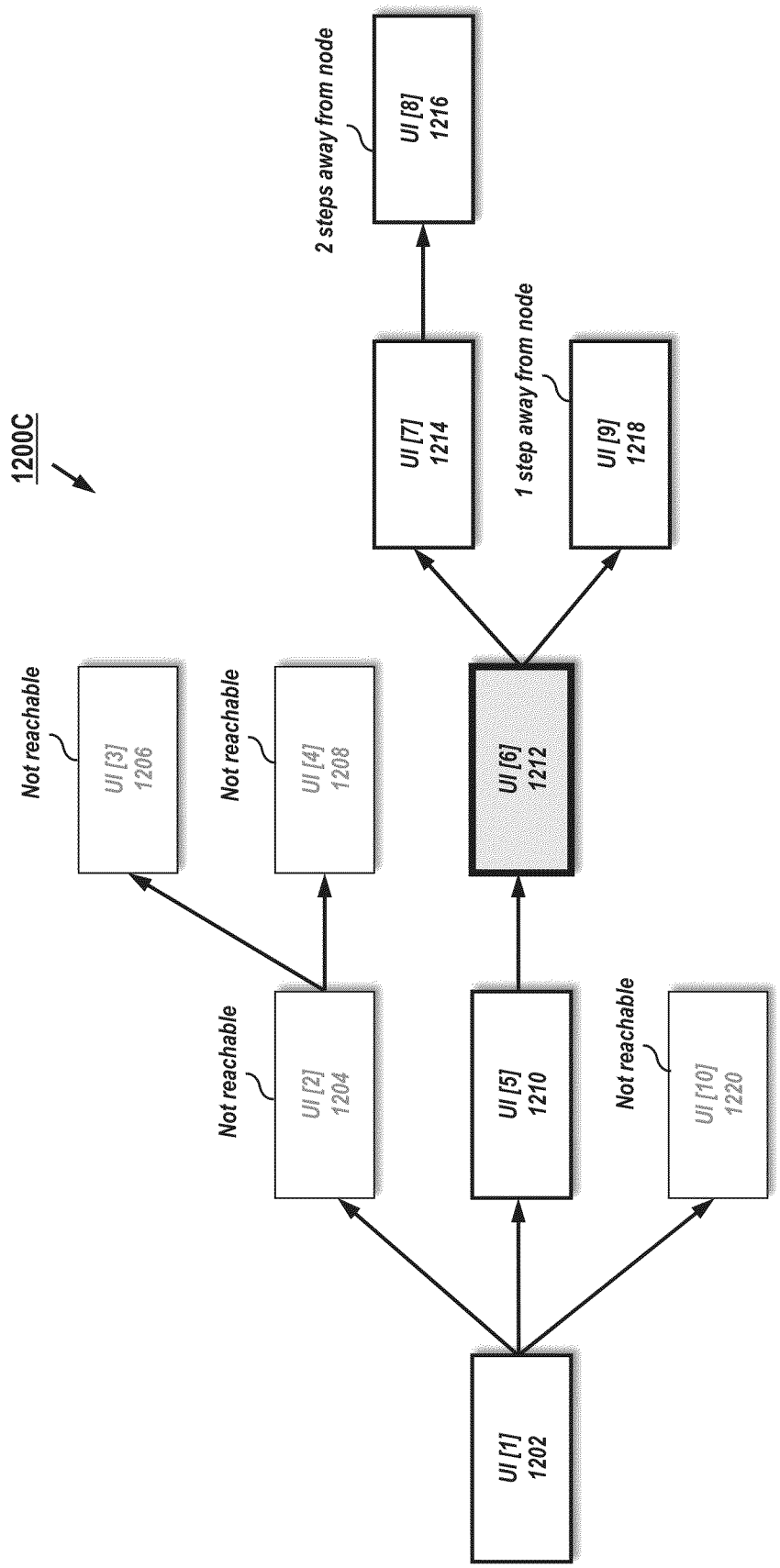
FIG. 12C show the workflow progression continuing from the embodiment of FIG. 12B with still further node processing under an illustrative embodiment.

Turning now to FIG. 12C, the drawing show the workflow progression (1200C) continuing from the embodiment of FIG. 12B with still further node processing under an illustrative embodiment. Here, after node UI[5] 1210 receives a predetermined data input, the workflow process moves to node UI[6] 1212, which becomes a current node in the process. As discussed above, the processing device still identifies the first branch ending at node UI[8] 1216 calculates that the end node UI[8] 1216 of the first branch is now two steps away from the current node (1212). The processing device may also identify other branches, such as the one ending at UI[9] 1218 and calculate that the end node UI[8] 1218 is one step away from the current node (1212).

Figure 12D:
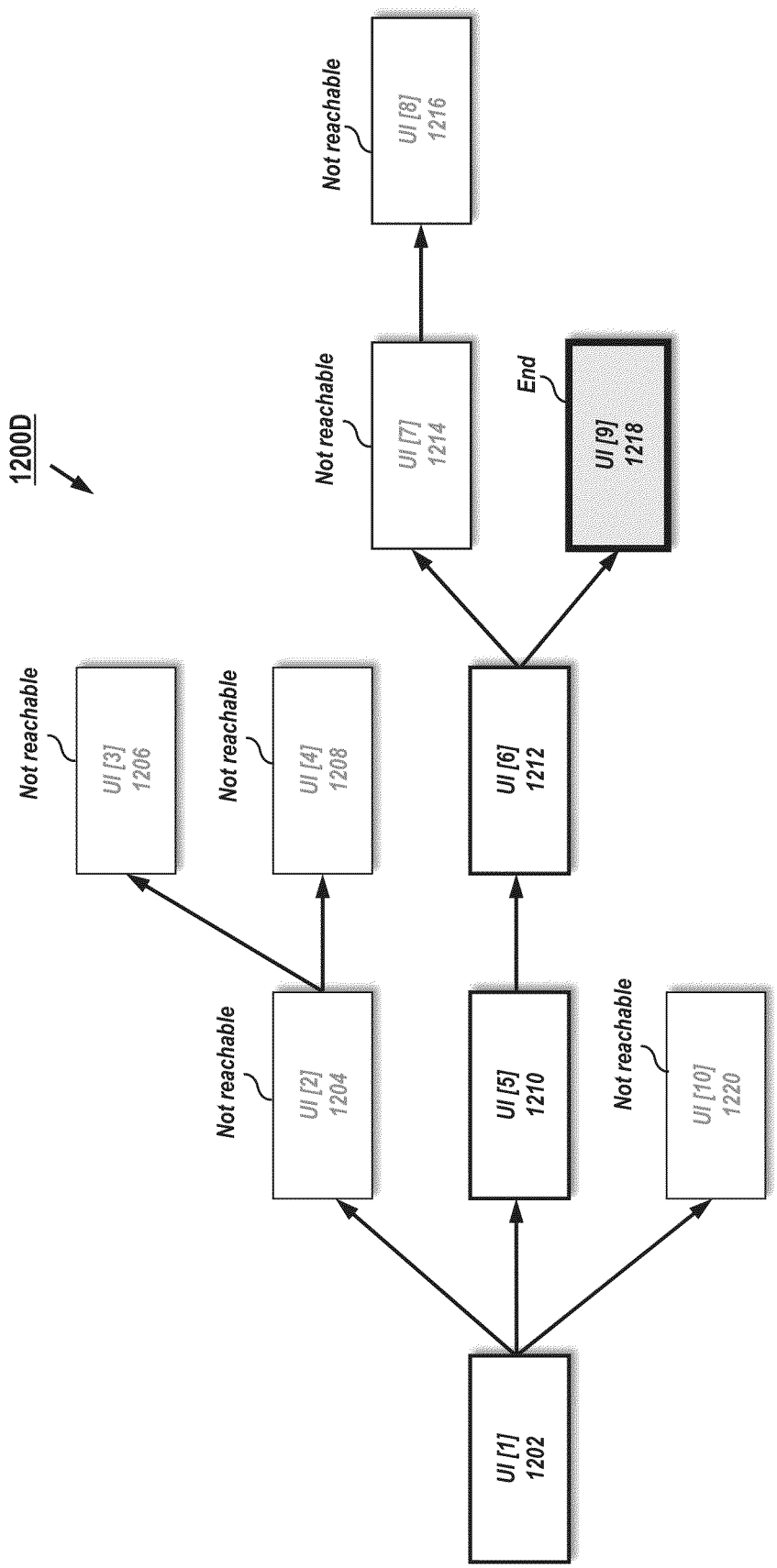
FIG. 12D show the workflow progression continuing from the embodiment of FIG. 12C with still further node processing under an illustrative embodiment.

FIG. 12D show the workflow progression 1200D continuing from the embodiment of FIG. 12C with still further node processing under an illustrative embodiment. Here, the node UI[6] 1212 receives a data input, the workflow process proceeds to node UI[9] 1218 which is determined to be the end node, at which point the processing device ends the existing workflow and executes an output or an algorithm. As the branch has proceeded to node 1202, the processing device also determines that the branch containing nodes 1214 and 1216 are not reachable. Under the present disclosure, during execution of workflow processes, a processing device (e.g., 202) may have an accurate estimation of progress within the workflow, and may adjust UIs depending on the estimated progress. For example, UIs may be configured to output specific data or additional data, depending on the workflow branch and level of progress. In another example, the physical appearance of the UIs may themselves be modified by coloring and/or shading UIs differently as the workflow progress is determined.

Figure 13:
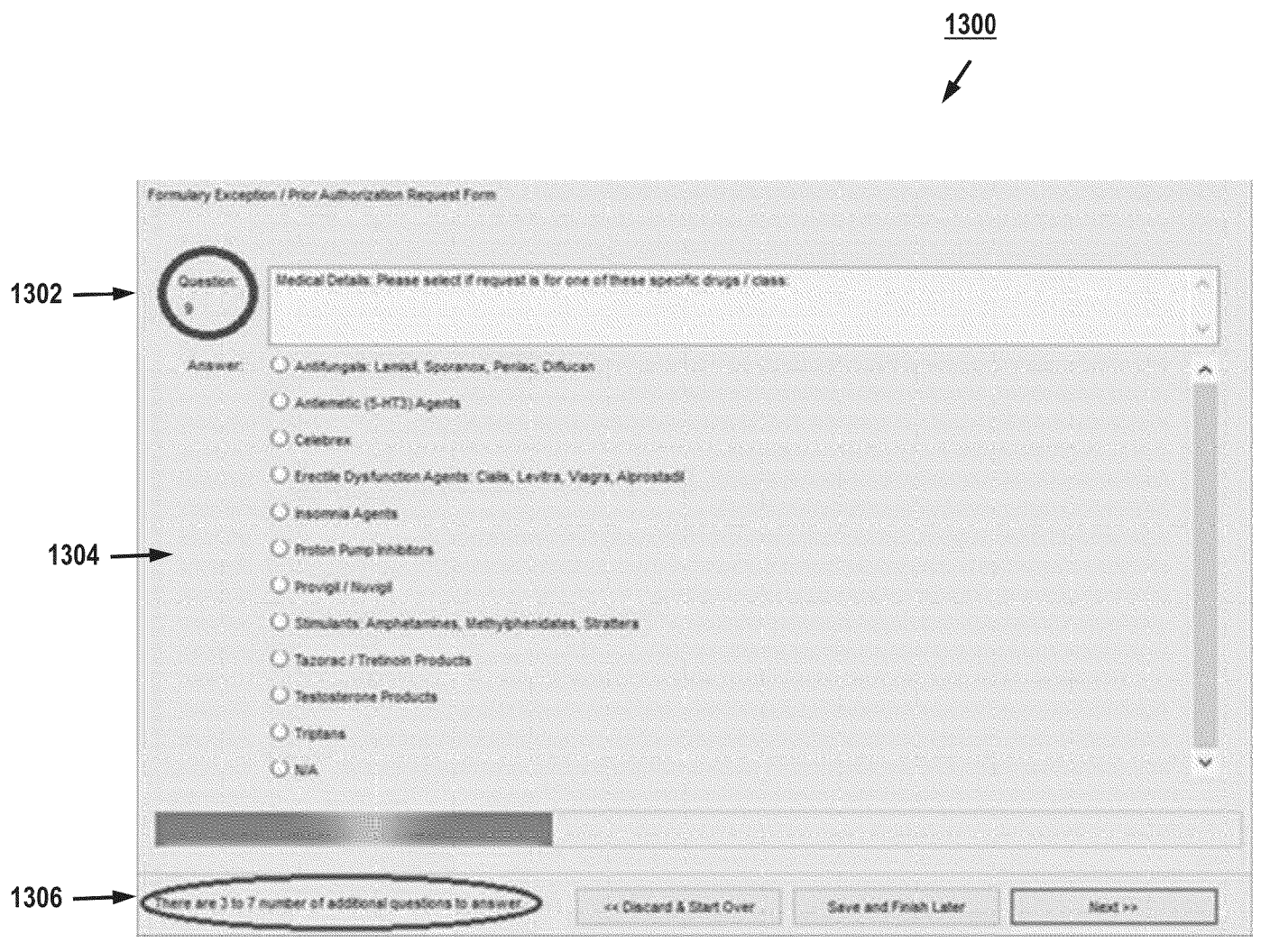
Figure 14:
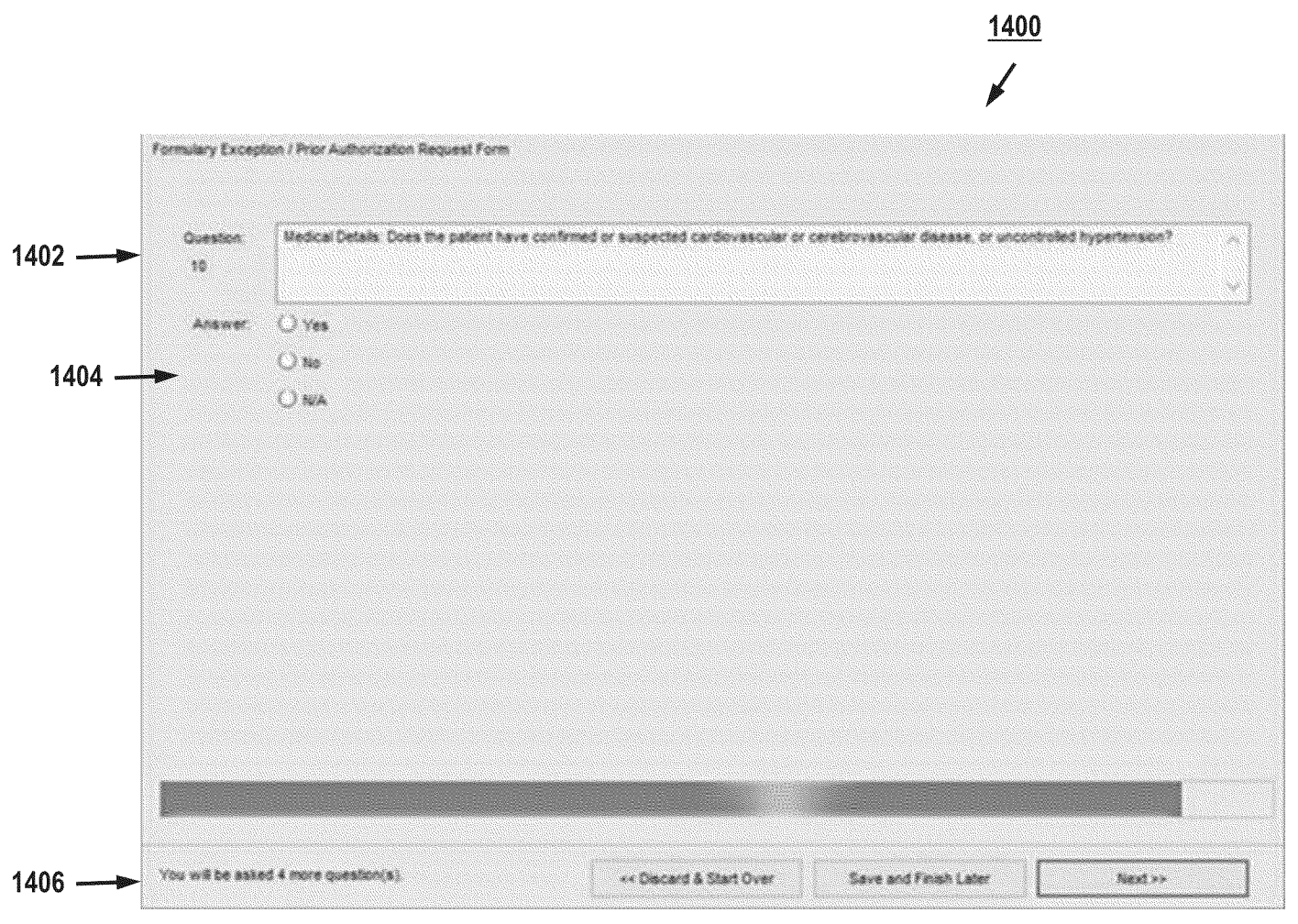

Of course, in addition to providing more efficient and/or effective UI operation, users of the system (e.g., 200) may have real-time estimates of workflow progress during use. FIG. 13 shows one example of a simulated screenshot 1300 providing feedback for future nodes under an illustrative embodiment. Using a medical questionnaire example, a portion of the UI may indicate a current node 1302 (Question 9) in which the workflow is executing, as well as data inputs (Answers) 1304, along with an estimated progress 1306. Similarly, FIG. 14 shows one example of another simulated screenshot 1400 providing feedback for future nodes under an illustrative embodiment. Similarly using a medical questionnaire example, a portion of the UI may indicate a current node 1402 (Question 10) in which the workflow is executing, as well as data inputs (Answers) 1404, along with an estimated progress 1406.

The figures and descriptions provided herein may have been simplified to illustrate aspects that are relevant for a clear understanding of the herein described devices, structures, systems, and methods, while eliminating, for the purpose of clarity, other aspects that may be found in typical similar devices, systems, and methods. Those of ordinary skill may thus recognize that other elements and/or operations may be desirable and/or necessary to implement the devices, systems, and methods described herein. But because such elements and operations are known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

Exemplary embodiments are provided throughout so that this disclosure is sufficiently thorough and fully conveys the scope of the disclosed embodiments to those who are skilled in the art. Numerous specific details are set forth, such as examples of specific components, devices, and methods, to provide this thorough understanding of embodiments of the present disclosure. Nevertheless, it will be apparent to those skilled in the art that specific disclosed details need not be employed, and that exemplary embodiments may be embodied in different forms. As such, the exemplary embodiments should not be construed to limit the scope of the disclosure. In some exemplary embodiments, well-known processes, well-known device structures, and well-known technologies may not be described in detail.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The disclosed embodiments may be implemented, in some cases, in hardware, firmware, software, or any tangibly-embodied combination thereof. The disclosed embodiments may also be implemented as instructions carried by or stored on one or more non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus for processing a user interface (UI) associated with a multi-nodal workflow in a medical software application, comprising:

a memory for storing the medical software application;

a processor, operatively coupled to the memory, wherein the processor is configured to generate the UI; and a workflow logic module, operatively coupled to the processor, wherein the workflow logic module is configured to process the medical software application to determine branches of the workflow, wherein each of the branches comprise one or more nodes configured to receive a data input and provide a corresponding data output for the medical software application during execution, execute serialization on at least some of the branches to determine dependencies among at least some of the nodes in the branches, monitor progress of the workflow during execution of the medical software application, based on the executed serialization, and provide feedback data associated with the monitored progress, process the determined branches of the workflow to identify non-reachable branches to remove the non-reachable branches during further monitoring of the workflow during execution of the medical software application, and update the UI in accordance with the monitored progress.

2. The apparatus of claim 1, wherein the workflow logic module is configured to execute serialization on the at least some of the branches by executing a depth-first serialization.

3. The apparatus of claim 1, wherein the workflow logic module is configured to execute serialization on the at least some of the branches by executing a breadth-first serialization.

4. The apparatus of claim 1, wherein the workflow logic module is configured to monitor progress of the workflow by identifying a current node and determining one or more branches of the workflow associated with the current node.

5. The apparatus of claim 4, wherein the workflow logic module is configured to determine the number of steps remaining in the workflow for an end node from the current node in the determined one or more branches of the workflow.

6. The apparatus of claim 5, wherein the workflow logic module is configured to provide the number of steps remaining in the workflow for an end node from the current node as feedback data associated with the monitored progress.

7. The apparatus of claim 1, wherein the data input comprises one of (i) data received via the UI via a peripheral device of the apparatus and (ii) sensor data.

8. A processor-based method for processing a user interface (UI) associated with a multi-nodal workflow in a medical software application, comprising:

storing the medical software application in a memory;

generating, via a processor, the UI;

generating, via a workflow logic module, the medical software application to determine branches of the workflow, wherein each of the branches comprise one or more nodes configured to receive a data input and provide a corresponding data output for the medical software application during execution;

executing, via the workflow logic module, serialization on at least some of the branches to determine dependencies among at least some of the nodes in the branches;

monitoring, via the workflow logic module, progress of the workflow during execution of the medical software application, based on the executed serialization, and provide feedback data associated with the monitored progress; and processing, via the workflow logic module, the determined branches of the workflow to identify non-reachable branches to remove the non-reachable branches during further monitoring of the workflow during execution of the medical software application, and updating the UI in accordance with the monitored progress.

9. The processor-based method of claim 8, wherein executing serialization on the at least some of the branches comprises executing a depth-first serialization.

10. The processor-based method of claim 8, wherein executing serialization on the at least some of the branches comprises executing a breadth-first serialization.

11. The processor-based method of claim 8, wherein monitoring progress of the workflow comprises identifying a current node and determining one or more branches of the workflow associated with the current node.

12. The processor-based method of claim 11, further comprising determining a number of steps remaining in the workflow for an end node from the current node in the determined one or more branches of the workflow.

13. The processor-based method of claim 12, further comprising providing the number of steps remaining in the workflow for an end node from the current node as feedback data associated with the monitored progress.

14. The processor-based method of claim 8, wherein the data input comprises one of (i) data received via the UI via a peripheral device of the apparatus and (ii) sensor data.

15. An apparatus for processing a user interface (UI) associated with a multi-nodal workflow in a medical software application, comprising:

a memory for storing the medical software application;

a processor, operatively coupled to the memory, wherein the processor is configured to generate the UI; and a workflow logic module, operatively coupled to the processor, wherein the workflow logic module is configured to process the medical software application to determine branches of the workflow, wherein each of the branches comprise one or more nodes configured to receive a data input and provide a corresponding data output for the medical software application during execution, execute serialization on at least some of the branches to determine dependencies among at least some of the nodes in the branches, wherein the serialization comprises one of depth-first or breadth-first serialization, monitor progress of the workflow during execution of the medical software application, based on the executed serialization, and provide feedback data associated with the monitored progress, process the determined branches of the workflow to identify non-reachable branches to remove the non-reachable branches during further monitoring of the workflow during execution of the medical software application, and update the UI in accordance with the monitored progress.

16. The apparatus of claim 15, wherein the workflow logic module is configured to monitor progress of the workflow by identifying a current node and determining one or more branches of the workflow associated with the current node.

17. The apparatus of claim 16, wherein the workflow logic module is configured to determine the number of steps remaining in the workflow for an end node from the current node in the determined one or more branches of the workflow.

18. The apparatus of claim 17, wherein the workflow logic module is configured to provide the number of steps remaining in the workflow for an end node from the current node as feedback data associated with the monitored progress.

19. The apparatus of claim 18, wherein the data input comprises one of (i) data received via the UI via a peripheral device of the apparatus and (ii) sensor data.

20. The apparatus of claim 15, wherein the apparatus comprises a computing device.

\* \* \* \* \*